United States Patent [19]
Godowski et al.

[11] Patent Number: 5,328,837
[45] Date of Patent: Jul. 12, 1994

[54] HEPATOCYTE GROWTH FACTOR PROTEASE DOMAIN VARIANTS

[75] Inventors: Paul J. Godowski, Pacifica; Natalie A. Lokker, San Francisco; Melanie R. Mark, San Jose, all of Calif.

[73] Assignee: Genentech, Inc., South San Francisco, Calif.

[21] Appl. No.: 885,971

[22] Filed: May 18, 1992

[51] Int. Cl.$^5$ .................... C12P 21/06; A61K 37/36
[52] U.S. Cl. ................... 435/69.4; 530/399; 536/23.51
[58] Field of Search .............. 530/399; 536/27; 435/23.51, 69.1, 69.4

[56] References Cited

U.S. PATENT DOCUMENTS 4,330,528  5/1982  Ruhenstroth-Bauer et al. .
4,341,765  7/1982  Ruhenstroth-Bauer et al. .
5,004,805  4/1991  Gohda et al. .

FOREIGN PATENT DOCUMENTS 287493   4/1988  European Pat. Off. .
412557   8/1990  European Pat. Off. .
450386   3/1991  European Pat. Off. .
456188   5/1991  European Pat. Off. .
461560   6/1991  European Pat. Off. .
462549   6/1991  European Pat. Off. .
492614  12/1991  European Pat. Off. .
2914903  4/1979  Fed. Rep. of Germany .
WO92/01053 7/1991  PCT Int'l Appl. .
WO92/05184 9/1991  PCT Int'l Appl. .

OTHER PUBLICATIONS

Matsumoto et al, 1991 Biochem. Biophys. Res. Commun. 181(2):691–699.
Gak, et al., "Processing of Hepatocyte Growth Factor to the Heterodimeric Form is Required for Biological Activity," FEBS Letters 311(1): 17–21 (1992).
Lokker, N. et al., "Structure-Function Analysis of Hepatocyte Growth Factor: Identification of Variants that Lack Mitogenic Activity Yet Retain High Affinity Receptor Binding," EMBO J. 11(7): 2503–2510 (1992).
Naka, D. et al., "Activation of Hepatocyte Growth Factor by Proteolytic Conversion of a Single Chain Form to a Heterodimer," J. Biol. Chem. 267(88): 20114–20119 (1992).
Seki, T. et al., "Isolation and Expression of cDNA for Different Forms of Hepatocyte Growth Factor from Human Leukocyte," Biochem. Biophys. Res. Comm. 172(1): 321–327 (1990).
Shima, N. et al., "Tumor Cytotoxic Factor/Hepatocyte Growth Factor from Human Fibroblasts: Cloning of Its cDNA, Purification and Characterization of Recombinant Protein," Biochem. Biophys. Res. Com. 180(2): 1151–1158 (1991).
Asami et al., J. Biochem. 109, 8–13 (1991).
Bottaro et al., Science 251, 802–804 (1991).
Chan et al., Science 254, 1382–1385 (1991).
Cooper et al., EMBO J. 5, 2623 (1986).
Giordano et al., Nature 339, 155 (1989).
Gohda et al., J. Clin. Invest. 81, 414–419 (1988).
Han et al., Biochem. 30, 9768–9780 (1991).
Igawa et al., Biochem. Biophys. Res. Commun. 174, 831–838 (1991).
Lindroos et al., Hepatol. 13, 734–750 (1991).
Matsumoto et al., Biochem. Biophys. Res. Commun. 176, 45–51 (1991).
Michalopoulos et al., Cancer Res. 44, 4414–4419 (1984).
Miyazawa et al., Eur. J. Biochem. 197, 15–22 (1991).
Miyazawa et al., Biochem. Biophys. Res. Comm. 163, 967–973 (1989).
Montesano et al., Cell 67, 901–908 (1991).
Nakamura et al., Biochem. Biophys. Res. Comm. 122, 1450–1459 (1984).

(List continued on next page.)

Primary Examiner—Robert J. Hill, Jr.
Assistant Examiner—K. Cochrane Carlson
Attorney, Agent, or Firm—Ginger R. Dreger

[57] ABSTRACT

The invention concerns hepatocyte growth factor (HGF) variants that compise an amino acid alteration at a site within the protease domain of HGF and retaining substantially full receptor binding affinity of the corresponding wild-type HGF.

21 Claims, 13 Drawing Sheets

OTHER PUBLICATIONS

Nakamura et al., *Proc. Natl. Acad. Sci. USA*, 83, 6489–6493 (1986).
Nakamura et al., *FEBS Letters* 224, 311–315 (1987).
Nakamura et al., *Nature* 342, 440–443 (1989).
Naldini et al., *Oncogene* 6, 501–504 (1991).
Naldini et al., *EMBO J.* 10, 2867–2878 (1991).
Okajima et al., *Eur. J. Biochem.* 193, 375–381 (1990).
Park et al., *Proc. Natl. Acad. Sci. USA* 84, 6379–6383 (1987).
Rubin et al., *Proc. Natl. Acad. Sci. USA* 88, 415–419 (1991).
Russel et al., *J. Cell Physiol.* 119, 183–182 (1984).
Stoker et al., *Nature* 327, 239–242 (1987).
Tashiro et al., *Proc. Natl. Acad. Sci. USA* 87, 3200–3204 (1990).
Weidner et al., *J. Cell Biol.* 111, 2097–2108 (1990).
Wiman, B., *Eur. J. Biochem.* 76: 129–137 (1977).
JP 4,183,394 (Abstract) Jun. 30, 1992.
JP 4,030,000 (Abstract) Jan. 31, 1992.
JP 4,120,097 (Abstract) Apr. 21, 1992.
JP 4,036,189 (Abstract) Feb. 6, 1992.
JP 3,255,096 (Abstract) Nov. 13, 1991.
JP 3,204,899 (Abstract) Sep. 6, 1991.
JP 3,130,091 (Abstract) Jun. 3, 1991.
JP 2,288,899 (Abstract) Nov. 28, 1990.
JP 2,002,213 (Abstract) Jan. 5, 1990.
JP 1,027,491 (Abstract) Jan. 30, 1989.
JP 64,003,199 (Abstract) Jan. 6, 1989.
JP 62 161,730 (Abstract) Jul. 17, 1987.
JP 62,045,530 (Abstract) (with English translation) Feb. 27, 1987.
JP 60,045,534 (Abstract) Mar. 12, 1985.
JP 60,243,019 (Abstract) Dec. 3, 1985.
JP 4,013,696 (Abstract) Jan. 17, 1992.
JP 58,062,116 (Abstract) Apr. 13, 1983.

><Modified RK5 derivative, insert Xho I into Hind III site; PJG
2/89>
<from Cori 86.3.18  fix DHFR acc I
<sequence of CMV enhancer/promoter, from Cell 41, 1985>
T><from pPMLCMV beginning to HindIII,enhancers and promoter>
TCGAGCTCGCCCGACATTGATTA
TTGACTAGTTATTAATAGTAATCAATTACGGGGTCATTAGTTCATAGCCC
ATATATGGAGTTCCGCGTTACATAACTTACGGTAAATGGCCCGCCTGGCT
GACCGCCCAACGACCCCGCCCATTGACGTCAATAATGACGTATGTTCCC
ATAGTAACGCCAATAGGGACTTTCCATTGACGTCAATGGGTGGAGTATTT
ACGGTAAACTGCCCACTTGGCAGTACATCAAGTGTATCATATGCCAAGTA
CGCCCCCTATTGACGTCAATGACGGTAAATGGCCCGCCTGGCATTATGCC
CAGTACATGACCTTATGGGACTTTCCTACTTGGCAGTACATCTACGTATT
AGTCATCGCTATTACCATGGTGATGCGGTTTTGGCAGTACATCAATGGGC
GTGGATAGCGGTTTGACTCACGGGGATTTCCAAGTCTCCACCCCATTGAC
GTCAATGGGAGTTTGTTTTGGCACCAAAATCAACGGGACTTTCCAAAATG
TCGTAACAACTCCGCCCCATTGACGCAAATGGGCGGTAGGCGTGTACGGT
GGGAGGTCTATATAAGCAGAGCTCGTTTAGTGAACCG
<Begin RNA>
TCAGATCGCCTGG
AGACGCCATCCACGCTGTTTTGACCTCCATAGAAGACACCGGGACCGATC
CAGCCTCCGCGGCCGGGAACGGTGCATTGGAACGCGGATTCCCCGTGCCA
AGAGTGACGTAAGTACCGCCTATAGAGTCTATAGGCCCACCCCCTTGGCT
T
><sp6 promoter>
<GGCCCACCCCCTTGGCTT>CGTTAGAACGCGGCTACAATTAATACATAACC
T T A T G T A T C A T A C A C A T A C G A T T T A G G T G A C A C T A T A><s p 6    RNA
start>GAATA<ACATCCACTTTGCCTTTC>

ACATCCACTTTGCCTTTCTCTCC
ACAGGTGTCCACTCCCAGGTCCAA<PstI-ClaI converter>CTGCA

>    <    c    l    o    n    i    n    g
linker>CCTCGGTTCTATCGATTGAATTCCCCGGGGATCCTCTAGAGTCGACCTGCAGAAGCTT
GCCTCGAGGCAAGCTT
GGCCGCCATGGCCC
><sv40 early poly A>AACTTGTTTATTGCAGCTTATAATGGTT
ACAAATAAAGCAATAGCATCACAAATTTCACAAATAAAGCATTTTTTTCACTGCATTCTA
GTTGTGGTTTGTCCAAACTCATCAATGTATCTTATCATGTCT
GGATCGATCGG
>        <        s        v        4        0
origin>GAATTAATTCGGCGCAGCACCATGGCCTGAAATAACCTCTGAAAGAGGAACTTGGTTA
GGTACCTTC
TGAGGCGGAAAGAACCAGCT
GTGGAATGTGTGTCAGTTAGGGTGTGGAAAGTCCCCAGGCTCCCCAGCAGGC
AGAAGTATGCAAAGCATGCATCTCAATTAGTCAGCAACCAGGTGTGGAAAGTCCCCAGGC
TCCCCAGCAGGCAGAAGTATGCAAAGCATGCATCTCAATTAGTCAGCAACCATAGTCCCG
CCCCTAACTCCGCCCATCCCGCCCCTAACTCCGCCCAGTTCCGCCCATTCTCCGCCCCAT
GGCTGACTAATTTTTTTTATTTATGCAGAGGCCGAGGCCGCCTCGGCCTCTGAGCTATTC
CAGAAGTAGTGAGGAGGCTTTTTTGGAGGCCTAGGCTTTTGCAAA
><start pUC118>
AAGCTGTTAACAGCTTGGC
ACTGGCCGTCGTTTTACAACGTCGTGACTGGGAAAACC
CTGGCGTTACCCAACTTAATCGCCTTGCAGCACATCCCCCCTTCGCCAGCTGGCGTAATA

FIG. 5A

```
GCGAAGAGGCCCGCACCGATCGCCCTTCCCAACAGTTGCGTAGCCTGAATGGCGAATGGC
<start M13>
G CCTGATGCGG
     TATTTTCTCC TTACGCATCT GTGCGGTATT TCACACCGCA TA CGTCAAAGCAACCATAGTACGCGCCCTGTAGCGGCGCATTAAGCGCGGCGGGTG
TGGTGGTTACGCGCAGCGTGACCGCTACACTTGCCAGCGCCCTAGCGCCCGCTCCTTTCG
CTTTCTTCCCTTCCTTTCTCGCCACGTTCGCCGGCTTTCCCCGTCAAGCTCTAAATCGGG
GGCTCCCTTTAGGGTTCCGATTTAGTGCTTTACGGCACCTCGACCCCAAAAAACTTGATT
TGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTA
TCTCGGGCTATTCTTTTGATTTATAAGGGATTTTGCCGATTTCGGCCTATTGGTTAAAAA
ATGAGCTGATTTAACAAAAATTTAACGCGAATTTTAACAAAATATTAACGTTTACAATTT TATGGTGCAC TCTCAGTACA
     ATCTGCTCTG ATGCCGCATA GTTAAGCCA           ACTCC GCTATCGCTA
CGTGACTGGG
     TCATGGCTGC GCCCCGACAC CCGCCAACAC CCGCTGACGC GCCCTGACGG
GCTTGTCTGC
     TCCCGGCATC CGCTTACAGA CAAGCTGTGA CCGTCTCCGG GAGCTGCATG
TGTCAGAGGT
     TTTCACCGTC ATCACCGAAA CGCGCGAGGC AG
TATTC
<             Hinc II (2271) to GTCATC>
<             Pst I (1973) to CTGCTG>
<             Acc I (183) delete 6 bp>
<Arbitrarily change EcoRI (1) to GAATAC>
<pUCx 83.11.25 sequence not fully known>
                TTGAAGACGA AAGGGCCTCG TGATACGCCT ATTTTTATAG
     GTTAATGTCA TGATAATAAT GGTTTCTTAG ACGTCAGGTG GCACTTTTCG
GGGAAATGTG
     CGCGGAACCC CTATTTGTTT ATTTTTCTAA ATACATTCAA ATATGTATCC
GCTCATGAGA
     CAATAACCCT GATAAATGCT TCAATAATAT TGAAAAAGGA AGAGTATGAG
TATTCAACAT
     TTCCGTGTCG CCCTTATTCC CTTTTTTGCG GCATTTTGCC TTCCTGTTTT
TGCTCACCCA
     GAAACGCTGG TGAAAGTAAA AGATGCTGAA GATCAGTTGG GTGCACGAGT
GGGTTACATC
     GAACTGGATC TCAACAGCGG TAAGATCCTT GAGAGTTTTC GCCCCGAAGA
ACGTTTTCCA
     ATGATGAGCA CTTTTAAAGT TCTGCTATGT GGCGCGGTAT TATCCCGTGA
TGACGCCGGG
     CAAGAGCAAC TCGGTCGCCG CATACACTAT TCTCAGAATG ACTTGGTTGA
GTACTCACCA
     GTCACAGAAA AGCATCTTAC GGATGGCATG ACAGTAAGAG AATTATGCAG
TGCTGCCATA
     ACCATGAGTG ATAACACTGC GGCCAACTTA CTTCTGACAA CGATCGGAGG
ACCGAAGGAG
     CTAACCGCTT TTTTGCACAA CATGGGGGAT CATGTAACTC GCCTTGATCG
TTGGGAACCG
     GAGCTGAATG AAGCCATACC AAACGACGAG CGTGACACCA CGATGCCAGC
AGCAATGGCA
     ACAACGTTGC GCAAACTATT AACTGGCGAA CTACTTACTC TAGCTTCCCG
```

FIG. 5B

```
GCAACAATTA
        ATAGACTGGA   TGGAGGCGGA   TAAAGTTGCA   GGACCACTTC   TGCGCTCGGC
CCTTCCGGCT
        GGCTGGTTTA   TTGCTGATAA   ATCTGGAGCC   GGTGAGCGTG   GGTCTCGCGG
TATCATTGCA
        GCACTGGGGC   CAGATGGTAA   GCCCTCCCGT   ATCGTAGTTA   TCTACACGAC
GGGGAGTCAG
        GCAACTATGG   ATGAACGAAA   TAGACAGATC   GCTGAGATAG   GTGCCTCACT
GATTAAGCAT
        TGGTAACTGT   CAGACCAAGT   TTACTCATAT   ATACTTTAGA   TTGATTTAAA
ACTTCATTTT
        TAATTTAAAA   GGATCTAGGT   GAAGATCCTT   TTTGATAATC   TCATGACCAA
AATCCCTTAA
        CGTGAGTTTT   CGTTCCACTG   AGCGTCAGAC   CCCGTAGAAA   AGATCAAAGG
ATCTTCTTGA
        GATCCTTTTT   TTCTGCGCGT   AATCTGCTGC   TTGCAAACAA   AAAAACCACC
GCTACCAGCG
        GTGGTTTGTT   TGCCGGATCA   AGAGCTACCA   ACTCTTTTTC   CGAAGGTAAC
TGGCTTCAGC
        AGAGCGCAGA   TACCAAATAC   TGTCCTTCTA   GTGTAGCCGT   AGTTAGGCCA
CCACTTCAAG
        AACTCTGTAG   CACCGCCTAC   ATACCTCGCT   CTGCTAATCC   TGTTACCAGT
GGCTGCTGCC
        AGTGGCGATA   AGTCGTGTCT   TACCGGGTTG   GACTCAAGAC   GATAGTTACC
GGATAAGGCG
        CAGCGGTCGG   GCTGAACGGG   GGGTTCGTGC   ACACAGCCCA   GCTTGGAGCG
AACGACCTAC
        ACCGAACTGA   GATACCTACA   GCGTGAGCAT   TGAGAAAGCG   CCACGCTTCC
CGAAGGGAGA
        AAGGCGGACA   GGTATCCGGT   AAGCGGCAGG   GTCGGAACAG   GAGAGCGCAC
GAGGGAGCTT
        CCAGGGGGAA   ACGCCTGGTA   TCTTTATAGT   CCTGTCGGGT   TTCGCCACCT
CTGACTTGAG
        CGTCGATTTT   TGTGATGCTC   GTCAGGGGGG   CGGAGCCTAT   GGAAAAACGC
CAGCAACGCG
        GCCTTTTTAC   GGTTCCTGGC   CTTTTGCTGG   CCTTTTGCTC   ACATGTTCTT
TCCTGCGTTA
        TCCCCTGATT   CTGTGGATAA   CCGTATTACC   GCCTTTGAGT   GAGCTGATAC
CGCTCGCCGC
        AGCCGAACGA   CCGAGCGCAG   CGAGTCAGTG   AGCGAGGAAG   CGGAAGAGC
<end M13>
GCCCAATACGCAA
ACCGCCTCTCCCCGCGCGTTGGCCGATTCATTAATCCAGCTGGCACGACAGGTTTCCCGA
CTGGAAAGCGGGCAGTGAGCGCAACGCAATTAATGTGAGTTACCTCACTCATTAGGCACC
CCAGGCTTTACACTTTATGCTTCCGGCTCGTATGTTGTGTGGAATTGTGAGCGGATAACA
ATTTCACACAGGAAACAGCTATGACCATGATTAC
GAATTAA
```

FIG. 5C

><pCIS.EBON
>< assembled by Steve Williams June 1989
><"poison-minus" pRK
><with EBNA-1, oriP, neoR
><polylinker sites: XhoI, HindIII, NotI ><CMV enhancer/promoter
T
TCGAGCTCGCCCGACATTGATTA
TTG<SpeI>ACTAGTTATTAATAGTAATCAATTACGGGGTCATTAGTTCATAGCCC
ATATATGGAGTTCCGCGTTACATAACTTACGGTAAATGGCCCGCCTGGCT
GACCGCCCAACGACCCCCGCCCATTGACGTCAATAATGACGTATGTTCCC
ATAGTAACGCCAATAGGGACTTTCCATTGACGTCAATGGGTGGAGTATTT
ACGGTAAACTGCCCACTTGGCAGTACATCAAGTGTATCATATGCCAAGTA
CGCCCCCTATTGACGTCAATGACGGTAAATGGCCCGCCTGGCATTATGCC
CAGTACATGACCTTATGGGACTTTCCTACTTGGCAGTACATCTACGTATT
AGTCATCGCTATTACCATGGTGATGCGGTTTTGGCAGTACATCAATGGGC
GTGGATAGCGGTTTGACTCACGGGGATTTCCAAGTCTCCACCCCATTGAC
GTCAATGGGAGTTTGTTTTGGCACCAAAATCAACGGGACTTTCCAAAATG
TCGTAACAACTCCGCCCCATTGACGCAAATGGGCGGTAGGCGTGTACGGT
GGGAGGTCTATATAAGCAGAGCTCGTTTAGTGAACCG
<Begin RNA>
TCAGATCGCCTGG
AGACGCCATCCACGCTGTTTTGACCTCCATAGAAGACACCGGGACCGATC
CAGCCTCCGCGGCCGGGAACGGTGCATTGGAACGCGGATTCCCCGTGCCA
AGAGTGACGTAAGTACCGCCTATAGAGTCTATAGGCCCACCCCCTTGGCT
T
><sp6 promoter>
<GGCCCACCCCCTTGGCTT>CGTTAGAACGCGGCTACAATTAATACATAACC
T T A T G T A T C A T A C A C A T A C G A T T T A G G T G A C A C T A T A><s p 6     RNA
start>GAATA<ACATCCACTTTGCCTTTC>

ACATCCACTTTGCCTTTCTCTCC
ACAGGTGTCCACTCCCAGGTCCAA<PstI-ClaI converter>CTGCA

><cloning linker>CCTCGGTTCT
ATCGATTCTCGA

<EcoRI/klenow>GAATTAATTC

AAGCTTGCGGCCGCAGCTT
GGCCGCCATGGCCC
><sv40 early poly A>AACTTGTTTATTGCAGCTTATAATGGTT
ACAAATAAAGCAATAGCATCACAAATTTCACAAATAAAGCATTTTTTTCACTGCATTCTA
GTTGTGGTTTGTCCAAACTCATCAATGTATCTTATCATGTCT
GGATCGATCGG
>              <            s          v         4             0
origin>GAATTAATTCGGCGCAGCACCATGGCCTGAAATAACCTCTGAAAGAGGAACTTGGTTA <KpnI>GGTACCTTC
TGAGGCGGAAAGAACCAGCT
GTGGAATGTGTGTCAGTTAGGGTGTGGAAAGTCCCCAGGCTCCCCAGCAGGC
AGAAGTATGCAAAGCATGCATCTCAATTAGTCAGCAACCAGGTGTGGAAAGTCCCCAGGC

FIG. 6A

TCCCCAGCAGGCAGAAGTATGCAAAGCATGCATCTCAATTAGTCAGCAACCATAGTCCCG
CCCCTAACTCCGCCCATCCCGCCCCTAACTCCGCCCAGTTCCGCCCATTCTCCGCCCCAT
GGCTGACTAATTTTTTTATTTATGCAGAGGCCGAGGCCGCCTCGGCCTCTGAGCTATTC
CAGAAGTAGTGAGGAGGCTTTTTTGGAGGCCTAGGCTTTTGCAAA
 <start pUC118>
AAGCTGTT<HpaI end from SW1>

><delta 3
 <PCR primer seq; PCR product was blunted & ligated in> CACGTGAT
<this is EcoRV site remnant>

<RI cassette: EBNA-oriP-tk term-NeoR-tk prom>
<4913 bp EcoRI-Bam from 220_2>
<EcoRI>
 GAATTCTCAT
 GTTTGACAGC TTATCATCGA TA ><EBNA-1>
 GATCCTCACA GGCCGCACCC AGCTTTTCTT CCGTTGCCCC AGTAGCATCT CTGTCTGGTG
 ACCTTGAAGA GGAAGAGGAG GGGTCCCGAG AATCCCCATC CCTACCGTCC AGCAAAAAGG
 GGGACGAGGA ATTTGAGGCC TGGCTTGAGG CTCAGGACGC AAATCTTGAG GATGTTCAGC
 GGGAGTTTTC CGGGCTGCGA GTAATTGGTG ATGAGGACGA GGATGGTTCG GAGGATGGGG
 AATTTTCAGA CCTGGATCTG TCTGACAGCG ACCATGAAGG GGATGAGGGT GGGGGGGCTG
 TTGGAGGGGG CAGGAGTCTG CACTCCCTGT ATTCACTGAG CGTCGTCTAA TAAAGATGTC
 TATTGATCTC TTTTAGTGTG AATCATGTCT GACGAGGGGC CAGGTACAGG ACCTGGAAAT
 GGCCTAGGAG AGAAGGGAGA CACATCTGGA CCAGAAGGCT CCGGCGGCAG TGGACCTCAA
 AGAAGAGGGG GTGATAACCA TGGACGAGGA CGGGGAAGAG GACGAGGACG AGGAGGCGGA
 AGACCAGGAG CCCCGGGCGG CTCAGGATCA GGGCCAAGAC ATAGAGATGG TGTCCGGAGA
 CCCCAAAAAC GTCCAAGTTG CATTGGCTGC AAAGGGACCC ACGGTGGAAC AGGAGCAGGA
 GCAGGAGCGG GAGGGGCAGG AGCAGGAGGG GCAGGAGCAG GAGGAGGGGC AGGAGCAGGA
 GGAGGGGCAG GAGGGGCAGG AGGGGCAGGA GGGGCAGGAG CAGGAGGAGG GCAGGAGCA
 GGAGGAGGGG CAGGAGGGGC AGGAGGGGCA GGAGCAGGAG GAGGGGCAGG AGCAGGAGGA
 GGGGCAGGAG GGCAGGAGC AGGAGGAGGG GCAGGAGGGG CAGGAGGGGC AGGAGCAGGA
 GGAGGGGCAG GAGCAGGAGG AGGGGCAGGA GGGGCAGGAG CAGGAGGAGG GCAGGAGGG
 GCAGGAGGGG CAGGAGCAGG AGGAGGGGCA GGAGCAGGAG GGGCAGGAGG GGCAGGAGGG
 GCAGGAGCAG GAGGGGCAGG AGCAGGAGGA GGGGCAGGAG GGGCAGGAGG GGCAGGAGCA
 GGAGGGGCAG GAGCAGGAGG GCAGGAGCA GGAGGGGCAG GAGGGGCAGG AGCAGGAGGA
 GGGGCAGGAG GGGCAGGAGC AGGAGGGGCA GGAGGGGCAG GAGGGGCAGG AGCAGGAGGA
 GGGGCAGGAG CAGGAGGGGC AGGAGGGGCA GGAGCAGGAG GGGCAGGAGC AGGAGGGGCA
 GGAGGGGCAG GAGCAGGAGG GGCAGGAGGG GCAGGAGCAG GAGGGGCAGG AGGGGCAGGA
 GCAGGAGGAG GGCAGGAGC AGGAGGGGCA GGAGCAGGAG GTGGAGGCCG GGTCGAGGA
 GGCAGTGGAG GCCGGGGTCG AGGAGGTAGT GGAGGCCGGG GTCGAGGAGG TAGTGGAGGC
 CGCCGGGGTA GAGGACGTGA AAGAGCCAGG GGGGAAGTC GTGAAAGAGC CAGGGGGAGA
 GGTCGTGGAC GTGGAGAAAA GAGGCCCAGG AGTCCCAGTA GTCAGTCATC ATCATCCGGG
 TCTCCACCGC GCAGGCCCCC TCCAGGTAGA AGGCCATTTT CCACCCTGT AGGGGAAGCC
 GATTATTTTG AATACCACCA AGAAGGTGGC CCAGATGGTG AGCCTGACGT GCCCCCGGGA
 GCGATAGAGC AGGGCCCCGC AGATGACCCA GGAGAAGGCC CAAGCACTGG ACCCCGGGGT
 CAGGGTGATG GAGGCAGGCG CAAAAAAGGA GGGTGGTTTG GAAAGCATCG TGGTCAAGGA
 GGTTCCAACC CGAAATTTGA GAACATTGCA GAAGGTTTAA GAGCTCTCCT GGCTAGGAGT
 CACGTAGAAA GGACTACCGA CGAAGGAACT TGGGTCGCCG GTGTGTTCGT ATATGGAGGT
 AGTAAGACCT CCCTTTACAA CCTAAGGCGA GGAACTGCCC TTGCTATTCC ACAATGTCGT
 CTTACACCAT TGAGTCGTCT CCCCTTTGGA ATGGCCCCTG ACCCGGCCC ACAACCTGGC
 CCGCTAAGGG AGTCCATTGT CTGTTATTTC ATGGTCTTTT TACAAACTCA TATATTTGCT
 GAGGTTTTGA AGGATGCGAT TAAGGACCTT GTTATGACAA AGCCCGCTCC TACCTGCAAT

FIG. 6B

```
ATCAGGGTGA CTGTGTGCAG CTTTGACGAT GGAGTAGATT TGCCTCCCTG GTTTCCACCT
ATGGTGGAAG GGGCTGCCGC GGAGGGTGAT GACGGAGATG ACGGAGATGA AGGAGGTGAT
GGAGATGAGG GTGAGGAAGG GCAGGAGTGA TGTAACTTGT TAGGAGACGC CCTCAATCGT
ATTAAAAGCC GTGTATTCCC CCGCACTAAA GAATAAATCC CCAGTAGACA TCATGCGTGC
TGTTGGTGTA TTTCTGGCCA TCTGTCTTGT CACCATTTTC GTCCTCCCAA CATGGGGCAA
TTGGGCATAC CCATGTTGTC ACGTCACTCA GCTCCGCGCT CAACACCTTC TCGCGTTGGA
AAACATTAGC GACATTTACC TGGTGAGCAA TCAGACATGC GACGGCTTTA GCCTGGCCTC
CTTAAATTCA CCTAAGAATG GGAGCAACCA
                        ><oriP>GCATGCAGGA AAAGGACAAG CAGCGAAAAT
TCACGCCCCC TTGGGAGGTG GCGGCATATG CAAAGGATAG CACTCCCACT CTACTACTGG
GTATCATATG CTGAC
><family of repeats>
             TGTAT ATGCATGAGG ATAGCATATG CTACCCGGAT ACAGATTAGG
ATAGCATATA CTACCCAGAT ATAGATTAGG ATAGCATATG CTACCCAGAT ATAGATTAGG
ATAGCCTATG CTACCCAGAT ATAAATTAGG ATAGCATATA CTACCCAGAT ATAGATTAGG
ATAGCATATG CTACCCAGAT ATAGATTAGG ATAGCCTATG CTACCCAGAT ATAGATTAGG
ATAGCATATG CTACCCAGAT ATAGATTAGG ATAGCATATG CTATCCAGAT ATTTGGGTAG
TATATGCTAC CCAGATATAA ATTAGGATAG CATATACTAC CCTAATCTCT ATTAGGATAG
CATATGCTAC CCGGATACAG ATTAGGATAG CATATACTAC CCAGATATAG ATTAGGATAG
CATATGCTAC CCAGATATAG ATTAGGATAG CCTATGCTAC CCAGATATAA ATTAGGATAG
CATATACTAC CCAGATATAG ATTAGGATAG CATATGCTAC CCAGATATAG ATTAGGATAG
CCTATGCTAC CCAGATATAG ATTAGGATAG CATATGCTAT CCAGATATTT GGGTAGTATA
TGCTACCC
><end family of repeats>
         AT GGCAACATTA GCCCACCGTG CTCTCAGCGA CCTCGTGAAT ATGAGGACCA
ACAACCCTGT GCTTGGCGCT CAGGCGCAAG TGTGTGTAAT TTGTCCTCCA GATCGCAGCA
ATCGCGCCCC TATCTTGGCC CGCCCACCTA CTTATGCAGG TATTCCCCGG GGTGCCATTA
GTGGTTTTGT GGGCAAGTGG TTTGACCGCA GTGGTTAGCG GGGTTACAAT CAGCCAAGTT
ATTACACCCT TATTTTACAG TCCAAAACCG CAGGGCGGCG TGTGGGGGCT GACGCGTGCC
CCCACTCCAC AATTTCAAAA AAAAGAGTGG CCACTTGTCT TTGTTTATGG GCCCCATTGG
CGTGGAGCCC CGTTTAATTT TCGGGGGTGT TAGAGACAAC CAGTGGAGTC CGCTGCTGTC
GGCGTCCACT CTCTTTCCCC TTGTTACAAA TAGAGTGTAA CAACATGGTT CACCTGTCTT
GGTCCCTGCC TGGGACACAT CTTAATAACC CCAGTATCAT ATTGCACTAG GATTATGTGT
TGCCCATAGC CATAAATTCG TGTGAGATGG ACATCCAGTC TTTACGGCTT GTCCCCACCC
CATGGATTTC TATTGTTAAA GATATTCAGA ATGTTTCATT CCTACACTAG TATTTATTGC
CCAAGGGGTT TGTGAGGGTT ATATTGGTGT CATAGCACAA TGCCACCACT GAACCCCCCG
TCCAAATTTT ATTCTGGGGG CGTCACCTGA AACCTTGTTT TCGAGCACCT CACATACACC
TTACTGTTCA CAACTCAGCA GTTATTCTAT TAGCTAAACG AAGGAGAATG AAGAAGCAGG
CGAAGATTCA GGAGAGTTCA CTGCCCGCTC CTTGATCTTC AGCCACTGCC CTTGTGACTA
AAATGGTTCA CTACCCTCGT GGAATCCTGA CCCCATGTAA ATAAAACCGT GACAGCTCAT
GGGGTGGGAG ATATCGCTGT TCCTTA
                ><dyad region>GGAC CCTTTTACTA ACCCTAATTC GATAGCATAT
GCTTCCCGTT GGGTAACATA TGCTATTGAA TTAGGGTTAG TCTGGATAGT ATATACTACT
ACCCGGGAAG CATATGCTA
              ><end dyad>C CCGTTTAGGG TTAACAAGGG GGCCTTATAA ACACTATTGC
TAATGCCCTC TTGAGGGTCC GCTTATCGGT AGCTACACAG GCCCCTCTGA TTGACGTTGG
TGTAGCCTCC CGTAGTCTTC CTGGGCCCCT GGGAGGTACA TGTCCCCCAG CATTGGTGTA
AGAGCTTCAG CCAAGAGTTA CACATAAAGG CAATGTTGTG TTGCAGTCCA CAGACTGCAA
AGTCTGCTCC AGGATGAAAG CCACTCAGTG TTGGCAAATG TGCACATCCA TTTATAAGGA
TGTCAACTAC AGTCAGAGAA CCCCTTTGTG TTTGGTCCCC CCCCGTGTCA CATGTGGAAC
AGGGCCCAGT TGGCAAGTTG TACCAACCAA CTGAAGGGAT TACATGCACT GCCCG
><end oriP>
                              ><HSV TK TERM 3'END>TGACC
AATACAAAAC AAAAGCGCTC CTCGTACCAG CGAAGAAGGG GCAGAGATGC CGTAGTCAGG
```

FIG. 6C

```
TTTAGTTCGT CCGGCGGC
><pUC12 SmaI-HaeIII polylinker>
                    GG G<Bam site is next>

<1.65 kb Bam-EcoRI frag from pkan2.pcr.bam>
GGATCC
><Bam site made by PCR>
GCCAGAAATCCGCGCGGTGGTTTTTGGGGGTCGG
GGGTGTTTGGCAGCCACAGACGCCCGGTGTTCGTGTCGCGCCAGTACATGCGGTCCATGC
CCAGGCCATCCAAAAACCATGGGTCTGTCTGCTCAGTCCAGTCGTGGACCTGACCCCACG
CAACGCCCAAAAGAATAACCCCCACGAACCATAAAGCATTCCCCATGGGGGACCCCGTCC
CTAACCCACGGGGCCCGTGGCTATGGCGGGCTTGCCGCCCCGACGTTGGCTGCGAGCCCT
GGGCCTTCACCCGAACTTGGGGGTTGGGGTGGGGAAAAGGAAGAAACGCGGGCGTATTGG
CCCCAATGGGGTCTCGGTGGGGTATCGACAGAGTGCCAGCCCTGGGACCGAACCCCGCGT
TTATGAACAAACGACCCAACACCCGTGCGTTTTATTCTGTCTTTTTATTGCCGTCATAGC
GCGGGTTCCTTCCGGTATTGTCTCCTTCCGTGTTTCAGTTAGCCTCCCCCATCT
<HSV1 tk terminater SmaI>

<following is EcoRI - SmaI from pKan2, rc>
><tn5 neomycin phosphotransferase gene>
 <BglII-Sma, rc>
<SmaI,AvaI>CCCGGGGTGGGCGAAGAACTCCAGCATGAGATCCCCGCGCT
GGAGGATCATCCAGCCGGCGTCCCGGAAAACGATTCCGAAGCCCAACCTTTCATAGAAGG
CGGCGGTGGAATCGAAATCTCGTGATGGCAGGTTGGGCGTCGCTTGGTCGGTCATTTCGA
ACCCCAGAGTCCCGCTCAGAAGAACTCGTCAAGAAGGCGATAGAAGGCGATGCGCTGCGA
ATCGGGAGCGGCGATACCGTAAAGCACGAGGAAGCGGTCAGCCCATTCGCCGCCAAGCTC
TTCAGCAATATCACGGGTAGCCAACGCTATGTCCTGATAGCGGTCCGCCACACCCAGCCG
GCCACAGTCGATGAATCCAGAAAAGCGGCCATTTTCCACCATGATATTCGGCAAGCAGGC
ATCGCCATGGGTCACGACGAGATCCTCGCCGTCGGGCATGCGCGCCTTGAGCCTGGCGAA
CAGTTCGGCTGGCGCGAGCCCCTGATGCTCTTCGTCCAGATCATCCTGATCGACAAGACC
GGCTTCCATCCGAGTACGTGCTCGCTCGATGCGATGTTTCGCTTGGTGGTCGAATGGGCA
GGTAGCCGGATCAAGCGTATGCAGCCGCCGCATTGCATCAGCCATGATGGATACTTTCTC
GGCAGGAGCAAGGTGAGATGACAGGAGATCCTGCCCCGGCACTTCGCCCAATAGCAGCCA
GTCCCTTCCCGCTTCAGTGACAACGTCGAGCACAGCTGCGCAAGGAACGCCCGTCGTGGC
CAGCCACGATAGCCGCGCTGCCTCGTCCTGCAGTTCATTCAGGGCACCGGACAGGTCGGT
CTTGACAAAAAGAACCGGGCGCCCCTGCGCTGACAGCCGGAACACGGCGGCATCAGAGCA
GCCGATTGTCTGTTGTGCCCAGTCATAGCCGAATAGCCTCTCCACCCAAGCGGCCGGAGA
ACCTGCGTGCAATCCATCTTGTTCAATCATGCGAAACGATCCTCATCCTGTCTCTTGATC ><tk promoter>
 <EcoRI-BglII, rc>
<BglII>AGATCTGCGGCACGCTGTTGACGCTGTTAAGCGGGTCGCTGCA
GGGTCGCTCGGTGTTCGAGGCCACACGCGTCACCTTAATATGCGAAGTGGACCTGGGACC
GCGCCGCCCCGACTGCATCTGCGTGTTCGAATTC<EcoRI>

<back to SW2 sequence; EcoRV site remnant>
A

><M13 ori>
          TCAAAGCAACCATAGTACGCGCCCTGTAGCGGCGCATTAAGCGCGGCGGGTG
TGGTGGTTACGCGCAGCGTGACCGCTACACTTGCCAGCGCCCTAGCGCCCGCTCCTTTCG
```

FIG. 6D

```
CTTTCTTCCCTTCCTTTCTCGCCACGTTCGCCGGCTTTCCCCGTCAAGCTCTAAATCGGG
GGCTCCCTTTAGGGTTCCGATTTAGTGCTTTACGGCACCTCGACCCCAAAAAACTTGATT
TGGGTGATGGTTCACGTAGTGGGCCATCGCCCTGATAGACGGTTTTCGCCCTTTGACGT
TGGAGTCCACGTTCTTTAATAGTGGACTCTTGTTCCAAACTGGAACAACACTCAACCCTA
TCTCGGGCTATTCTTTTGATTTATAAGGGATTTTGCCGATTTCGGCCTATTGGTTAAAAA
ATGAGCTGATTTAACAAAAATTTAACGCGAATTTTAACAAAATATTAACGTTTACAATTT
```

TATGGTGCA<ApaLI/blunt>

><delta 2a>

```
                      <EcoO109I/blunt>GGCCTCG    TGATACGCCT
ATTTTTATAG
        GTTAATGTCA  TGATAATAAT  GGTTCTTAG   ACGTCAGGTG   GCACTTTTCG
GGGAAATGTG
        CGCGGAACCC  CTATTTGTTT  ATTTTTCTAA  ATACATTCAA   ATATGTATCC
GCTCATGAGA
        CAATAACCCT  GATAAATGCT  TCAATAATAT  TGAAAAAGGA   AGAGTATGAG
TATTCAACAT
        TTCCGTGTCG  CCCTTATTCC  CTTTTTTGCG  GCATTTTGCC   TTCCTGTTTT
TGCTCACCCA
        GAAACGCTGG  TGAAAGTAAA  AGATGCTGAA  GATCAGTTGG   GTGCACGAGT
GGGTTACATC
        GAACTGGATC  TCAACAGCGG  TAAGATCCTT  GAGAGTTTTC   GCCCCGAAGA
ACGTTTTCCA
        ATGATGAGCA  CTTTTAAAGT  TCTGCTATGT  GGCGCGGTAT   TATCCCGTGA
TGACGCCGGG
        CAAGAGCAAC  TCGGTCGCCG  CATACACTAT  TCTCAGAATG   ACTTGGTTGA
GTACTCACCA
        GTCACAGAAA  AGCATCTTAC  GGATGGCATG  ACAGTAAGAG   AATTATGCAG
TGCTGCCATA
        ACCATGAGTG  ATAACACTGC  GGCCAACTTA  CTTCTGACAA   CGATCGGAGG
ACCGAAGGAG
        CTAACCGCTT  TTTTGCACAA  CATGGGGGAT  CATGTAACTC   GCCTTGATCG
TTGGGAACCG
        GAGCTGAATG  AAGCCATACC  AAACGACGAG  CGTGACACCA   CGATGCCAGC
AGCAATGGCA
        ACAACGTTGC  GCAAACTATT  AACTGGCGAA  CTACTTACTC   TAGCTTCCCG
GCAACAATTA
        ATAGACTGGA  TGGAGGCGGA  TAAAGTTGCA  GGACCACTTC   TGCGCTCGGC
CCTTCCGGCT
        GGCTGGTTTA  TTGCTGATAA  ATCTGGAGCC  GGTGAGCGTG   GGTCTCGCGG
TATCATTGCA
        GCACTGGGGC  CAGATGGTAA  GCCCTCCCGT  ATCGTAGTTA   TCTACACGAC
GGGGAGTCAG
        GCAACTATGG  ATGAACGAAA  TAGACAGATC  GCTGAGATAG   GTGCCTCACT
GATTAAGCAT
        TGGTAACTGT  CAGACCAAGT  TTACTCATAT  ATACTTTAGA   TTGATTTAAA
ACTTCATTTT
        TAATTTAAAA  GGATCTAGGT  GAAGATCCTT  TTTGATAATC   TCATGACCAA
AATCCCTTAA
        CGTGAGTTTT  CGTTCCACTG  AGCGTCAGAC  CCCGTAGAAA   AGATCAAAGG
ATCTTCTTGA
        GATCCTTTTT  TTCTGCGCGT  AATCTGCTGC  TTGCAAACAA   AAAAACCACC
```

FIG. 6E

```
GCTACCAGCG
        GTGGTTTGTT   TGCCGGATCA   AGAGCTACCA   ACTCTTTTTC   CGAAGGTAAC
TGGCTTCAGC
        AGAGCGCAGA   TACCAAATAC   TGTCCTTCTA   GTGTAGCCGT   AGTTAGGCCA
CCACTTCAAG
        AACTCTGTAG   CACCGCCTAC   ATACCTCGCT   CTGCTAATCC   TGTTACCAGT
GGCTGCTGCC
        AGTGGCGATA   AGTCGTGTCT   TACCGGGTTG   GACTCAAGAC   GATAGTTACC
GGATAAGGCG
        CAGCGGTCGG   GCTGAACGGG   GGGTTCGTGC   ACACAGCCCA   GCTTGGAGCG
AACGACCTAC
        ACCGAACTGA   GATACCTACA   GCGTGAGCAT   TGAGAAAGCG   CCACGCTTCC
CGAAGGGAGA
        AAGGCGGACA   GGTATCCGGT   AAGCGGCAGG   GTCGGAACAG   GAGAGCGCAC
GAGGGAGCTT
        CCAGGGGGAA   ACGCCTGGTA   TCTTTATAGT   CCTGTCGGGT   TTCGCCACCT
CTGACTTGAG
        CGTCGATTTT   TGTGATGCTC   GTCAGGGGGG   CGGAGCCTAT   GGAAAAACGC   CAG
><delta1.PVU>
 <PvuII site introduced by mutagenesis; 228 bp PvuII fragment
deleted>
 <join to PvuII at 4532 in RK5>
                                              CTGGCACGACAGGTTTCCCGA
CTGGAAAGCGGGCAGTGAGCGCAACGCAATTAATGTGAGTTACCTCACTCATTAGGCACC
CCAGGCTTTACACTTTATGCTTCCGGCTCGTATGTTGTGTGGAATTGTGAGCGGATAACA
ATTTCACACAGGAAACAGCTATGACCATGATTAC
GAATTAA
```

FIG. 6F

HEPATOCYTE GROWTH FACTOR PROTEASE DOMAIN VARIANTS

BACKGROUND OF THE INVENTION

I. Field of the Invention

The present invention concerns amino acid sequence variants of hepatocyte growth factor (HGF), methods and means for preparing such variants, and pharmaceutical compositions comprising them.

II. Description of Background and Related Art

HGF was identified initially as a mitogen for hepatocytes [Michalopoulos et al., *Cancer Res.* 44, 4414–4419 (1984); Russel et al., *J. Cell. Physiol.* 119, 183–192 (1984) and Nakamura et al., *Biochem. Biophys. Res. Comm.* 122: 1450–1459 (1984)]. Nakamura et al., Supra reported the purification of HGF from the serum of partially hepatectomized rats. Subsequently, HGF was purified from rat platelets, and its subunit structure was determined [Nakamura et al., *Proc. Natl. Acad. Sci. USA,* 83, 6489–6493 (1986); and Nakamura et al., *FEBS Letters* 224, 311–316 (1987)]. The purification of human HGF (huHGF) from human plasma was first described by Gohda et al., *J. Clin. Invest.* 81, 414–419 (1988).

Both rat HGF and huHGF have been molecularly cloned, including the cloning and sequencing of a naturally occurring variant lacking 5 amino acids designated "delta5 HGF" [Miyazawa et al., *Biochem. Biophys. Res. Comm.* 163, 967–973 (1989); Nakamura et al., *Nature* 342, 440–443 (1989); Seki et al, *Biochem. and Biophys. Res. Commun.* 172, 321–327 (1990); Tashiro et al., *Proc. Natl. Acad. Sci. USA* 87, 3200–3204 (1990); Okajima et al., *Eur. J. Biochem.* 193, 375–381 (1990)].

The mature form of huHGF, corresponding to the major form purified from human serum, is a disulfide linked heterodimer derived by proteolytic cleavage of the human pro-hormone between amino acids R494 and V495. This cleavage process generates a molecule composed of an α-subunit of 440 amino acids ($M_r$ 69 kDa) and a β-subunit of 234 amino acids ($M_r$ 34 kDa). The nucleotide sequence of the hHGF cDNA reveals that both the α- and the β-chains are contained in a single open reading frame coding for a pre-pro precursor protein. In the predicted primary structure of mature hHGF, an interchain S-S bridge is formed between Cys 487 of the α-chain and Cys 604 in the g-chain (see Nakamura et al., *Nature,* supra). The N-terminus of the a-chain is preceded by 54 amino acids, starting with a methionine group. This segment includes a characteristic hydrophobic leader (signal) sequence of 31 residues and the prosequence. The a-chain starts at amino acid (aa) 55, and contains four Kringle domains. The Kringle 1 domain extends from about aa 128 to about aa 206, the Kringle 2 domain is between about aa 211 and about aa 288, the Kringle 3 domain is defined as extending from about aa 303 to about aa 383, and the Kringle 4 domain extends from about aa 391 to about aa 464 of the α-chain. It will be understood that the definition of the various Kringle domains is based on their homology with kringle-like domains of other proteins (prothrombin, plasminogen), therefore, the above limits are only approximate. As yet, the function of these Kringles has not been determined. The β-chain of huHGF shows high homology to the catalytic domain of serine proteases (38% homology to the plasminogen serine protease domain). However, two of the three residues which form the catalytic triad of serine proteases are not conserved in huHGF. Therefore, despite its serine protease-like domain, hHGF appears to have no proteolytic activity and the precise role of the β-chain remains unknown. HGF contains four putative glycosylation sites, which are located at positions 294 and 402 of the α-chain and at positions 566 and 653 of the β-chain.

In a portion of cDNA isolated from human leukocytes in-frame deletion of 15 base pairs was observed. Transient expression of the cDNA sequence in COS-1 cells revealed that the encoded HGF molecule (delta5 HGF) lacking 5 amino acids in the Kringle 1 domain was fully functional (Seki et al., supra).

A naturally occurring huHGF variant has recently been identified which corresponds to an alternative spliced form of the huHGF transcript containing the coding sequences for the N-terminal finger and first two kringle domains of mature huHGF [Chan et al., *Science* 254, 1382–1385 (1991); Miyazawa et al., *Eur. J. Biochem.* 197, 15–22 (1991)]. This variant, designated HGF/NK2, has been proposed to be a competitive antagonist of mature huHGF.

The comparison of the amino acid sequence of rat HGF with that of huHGF revealed that the two sequences are highly conserved and have the same characteristic structural features. The length of the four Kringle domains in rat HGF is exactly the same as in huHGF. Furthermore, the cysteine residues are located in exactly the same positions; an indication of similar three-dimensional structures (Okajima et al., supra; Tashiro et al., supra).

The HGF receptor has been identified as the product of the c-Met proto-oncogene [Bottaro et al., *Science* 251, 802–804 (1991); Naldini et al., *Oncogene* 6, 501–504 (1991)], an 190-kDa heterodimeric (a disulfide-linked 50-kDa α-chain and a 145-kDa β-chain) membrane-spanning tyrosine kinase protein [Park et al., *Proc. Natl. Acad. Sci. USA* 84, 6379–6383 (1987)]. The c-Met protein becomes phosphorylated on tyrosine residues of the 145-kDa β-subunit upon HGF binding.

The levels of HGF increase in the plasma of patients with hepatic failure (Gohda et al., supra) and in the plasma [Lindroos et al., *Hepatol.* 13, 734–750 (1991)] or serum [Asami et al., *J. Biochem.* 109, 8–13 (1991)] of animals with experimentally induced liver damage. The kinetics of this response is rapid, and precedes the first round of DNA synthesis during liver regeneration suggesting that HGF may play a key role in initiating this process. More recently, HGF has been shown to be a mitogen for a variety of cell types including melanocytes, renal tubular cells, keratinocytes, certain endothelial cells and cells of epithelial origin [Matsumoto et al., *Biochem. Biophys. Res. Commun.* 176, 45–51 (1991); Igawa et al., *Biochem. Biophys. Res. Commun.* 174, 831–838 (1991); Han et al., *Biochem.* 30, 9768–9780 (1991); Rubin et al., *Proc. Natl. Acad. Sci. USA* 88, 415–419 (1991)]. Interestingly, HGF can also act as a "scatter factor", an activity that promotes the dissociation of epithelial and vascular endothelial cells in vitro [Stoker et al., *Nature* 327, 239–242 (1987); Weidner et al., *J. Cell Biol.* 111, 2097–2108 (1990); Naldini et al., *EMBO J.* 10, 2867–2878 (1991)]. Moreover, HGF has recently been described as an epithelial morphogen [Montesano et al., *Cell* 67, 901–908 (1991)]. Therefore, HGF has been postulated to be important in tumor invasion and in embryonic development. Chronic c-Met/HGF receptor activation has been observed in certain malignancies [Cooper et al., *EMBO J.* 5, 2623 (1986); Giordano et al., *Nature* 339, 155 (1989)].

It would be desirable to better understand the structure-activity relationship of HGF in order to identify functionally important domains in the HGF amino acid sequence.

It would be particularly desirable to identify the amino acid residues which are responsible for the interaction of HGF with its receptor.

It would be also desirable to identify the amino acid residues which are responsible for HGF biological activity.

It would further be desirable to provide amino acid sequence variants of HGF that have altered (preferably enhanced) receptor binding affinity as compared to the corresponding mature, wild-type HGF.

It would also be desirable to provide HGF amino acid sequence variants which have retained or enhanced receptor binding affinity as compared to the corresponding wild-type HGF, but are substantially devoid of HGF biological activity. Such molecules could act as competitive antagonists of HGF action.

It would further be desirable to provide HGF amino acid sequence variants that have retained or enhanced receptor binding affinity and substantially retained or increased biological activity as compared to the corresponding wild-type HGF (HGF agonists).

Accordingly, it is an object of the present invention to provide HGF variants having retained or improved the receptor binding affinity of the corresponding mature wild-type HGF.

It is another object of the invention to provide HGF variants that have retained substantially full receptor binding affinity of the corresponding mature wild-type HGF and are substantially incapable of HGF receptor activation.

It is a further object to provide HGF variants that have retained substantially full receptor binding affinity of the corresponding mature wild-type HGF and have improved biological properties.

These and further objects will be apparent to one of ordinary skill in the art.

SUMMARY OF THE INVENTION

The foregoing objects are achieved by the provision of HGF variants having an amino acid alteration at a site within the protease domain of HGF and retaining substantially full receptor binding affinity of the corresponding wild-type HGF.

In a specific embodiment, the variants have substantially retained or improved receptor binding affinity as compared to the corresponding wild-type HGF, and are substantially devoid of HGF biological activity. Such compounds, if present in sufficient concentration, will act as competitive antagonists of HGF action.

In another specific embodiment, the variants combine substantially retained or improved receptor binding affinity with improved biological activity, as compared to the corresponding wild-type HGF. Such variants are valuable as HGF agonists.

In a preferred embodiment, the variants of the present invention comprise an alteration in a region corresponding to the catalytic site of serine proteases. More preferably the alteration is at or adjacent to any of positions 534, 673 and 692 of the wild-type human HGF (huHGF) amino acid sequence.

The alteration preferably is substitution.

In a particularly preferred embodiment, at least two of the residues at amino acid positions 534, 673 and 692 of the wild-type huHGF sequence are replaced by another amino acid.

In a preferred group of the HGF variants herein, both tyrosine (Y) at position 673 and valine (V) at position 692 of the huHGF sequence are replaced by another amino acid. This alteration potentially yields HGF variants which substantially retain the receptor binding affinity of wild-type huHGF but are substantially devoid of HGF biological activity.

Variants which have retained the ability to bind a native HGF receptor but show significantly reduced HGF biological activity may be further altered to improve the affinity of receptor binding. Such further alterations may be at or around the one-chain to two-chain cleavage site of the HGF molecule, and preferably at one or more of amino acid positions 493, 494, 495 and 496 of the wild-type huHGF amino acid sequence. The resultant variants are resistant to proteolytic cleavage by enzymes that are capable of in vivo conversion of HGF into its two-chain, biologically active form.

Other variants may have alterations within the kringle domains and/or at the C-terminal end, in addition to the alterations in the protease domain.

In all embodiments, huHGF amino acid sequence variants are preferred.

In other embodiments, the invention relates to DNA sequences encoding the variants described above, replicable expression vectors containing and capable of expressing such DNA sequences in a transformed host cell, transformed host cells, and a process comprising culturing the host cells so as to express the DNAs encoding the HGF variants.

In yet another embodiment, the invention relates to therapeutic compositions comprising HGF variants having HGF antagonist or agonist properties.

BRIEF DESCRIPTION OF THE DRAWINGS

FIGS. 5A, 5B and 5C depict progressive portions of the nucleotide sequence encoding the plasmid pRK5.1 (SEQ. ID. NO: 1).

FIGS. 6A, 6B, 6C, 6D, 6E and 6F depict progressive portions of the nucleotide sequence encoding the plasmid p.CIS.EBON (SEQ. ID. NO: 15).

DETAILED DESCRIPTION OF THE INVENTION

I. Definitions

Figure 1:
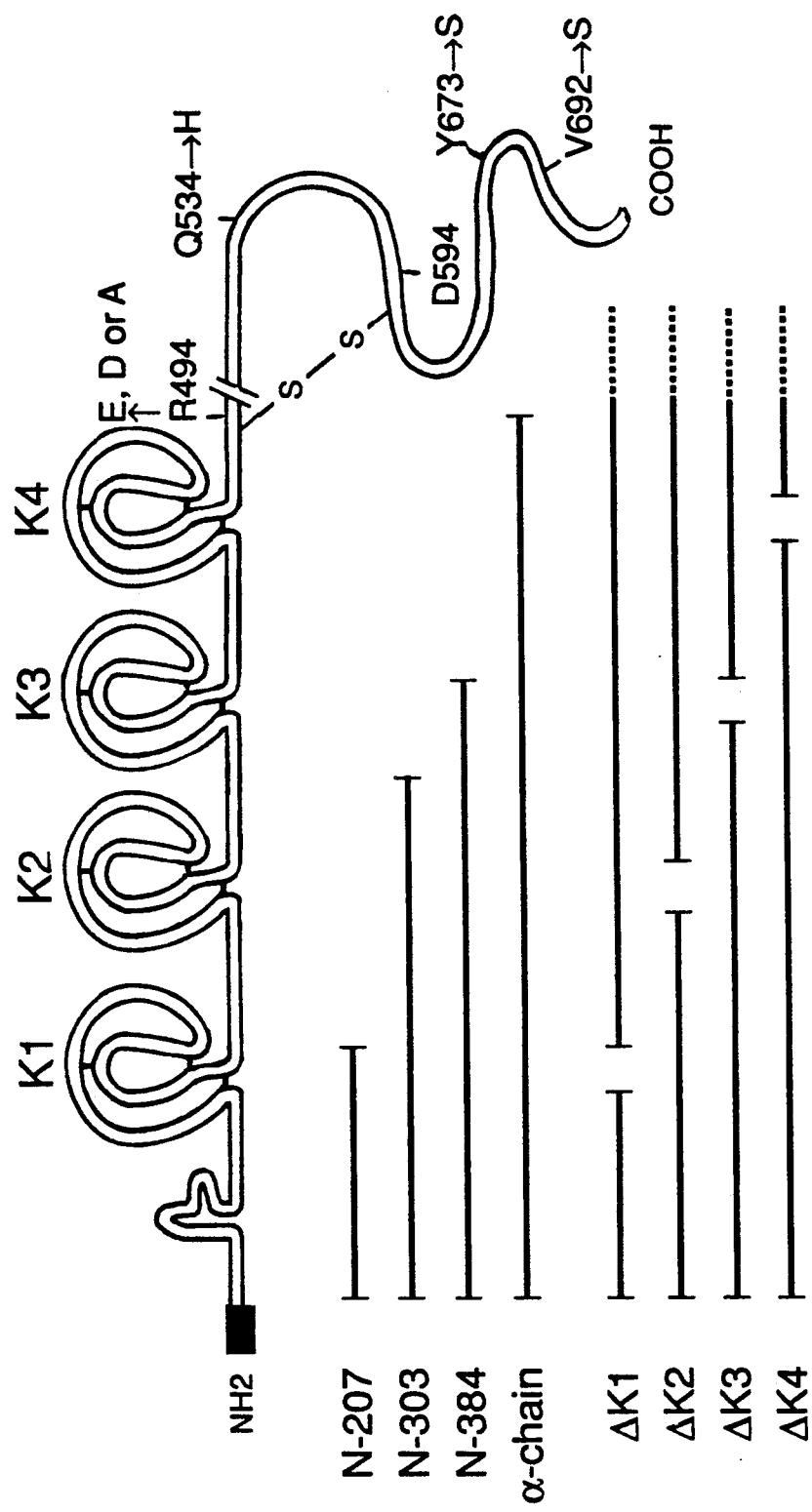
FIG. 1 is a schematic representation of the α- and β-subunits of huHGF. Shown in the α-chain are the signal sequence (boxed region) which encompasses amino acids 1–31, the predicted finger and four Kringle domains, each with their respective three disulfide bonds. The cleavage site for generation of the heterodimeric α/β form of huHGF immediately follows the P1 cleavage residue R494. This last residue has been specifically substituted with either E, D or A to generate HGF single-chain variants. The β-chain, which follows the cleavage site, contains homology to serine proteases. It is proposed that the α- and β-chains are held together by a unique disulfide-bridge between C487(α) and C604(β) (Nakamura et al., 1989, supra). Three residues within the β-chain have been substituted individually or in combination to reconstitute the authentic residues of a serine-protease. Schematic representations of the mature forms of the C-terminal truncation variants are depicted below: N-207, deleted after the first Kringle; N-303, deleted after the second Kringle; N-384, deleted after the third Kringle and the α-chain. Also shown are the variants where deletions of each of the Kringles (ΔK1, ΔK2, ΔK3 and ΔK4) were introduced. In each case, the deletions specifically remove the entire Kringle from C1 to C6.

As used herein, the terms "hepatocyte growth factor", "HGF" and "huHGF" refer to a (human) growth factor capable of specific binding to a receptor of wild-type (human) HGF, which growth factor typically has a structure with six domains (finger, Kringle 1, Kringle 2, Kringle 3, Kringle 4 and serine protease domains), but nonetheless may have fewer domains or may have some of its domains repeated if it still retains its qualitative HGF receptor binding ability. This definition specifically includes the delta5 huHGF as disclosed by Seki et al., supra. The terms "hepatocyte growth factor" and "HGF" also include hepatocyte growth factor from any non-human animal species, and in particular rat HGF.

The terms "wild-type human hepatocyte growth factor", "native human hepatocyte growth factor", "wild-type huHGF", and "native huHGF" refer to native sequence human HGF, i.e., that encoded by the cDNA sequence published by Miyazawa, et al. 1989, supra, or Nakamura et al., 1989, supra, including its mature, pre, pre-pro, and pro forms, purified from natural source, chemically synthesized or recombinantly produced. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms as defined for the purpose of the present invention. It will be understood that natural allelic variations exist and can occur among individuals, as demonstrated by one or more amino acid differences in the amino acid sequence of each individual. Amino acid positions in the variant huHGF molecules herein are indicated in accordance with the numbering of Miyazawa et al. 1989, supra.

The terms "(HGF) biological activity", "biologically active", "activity" and "active" refer to any mitogenic, motogenic or morphogenic activities exhibited by wild-type human HGF. The HGF biological activity may, for example, be determined in an in vitro or in vivo assay of hepatocyte growth promotion. Adult rat hepatocytes in primary culture have been extensively used to search for factors that regulate hepatocyte proliferation. Accordingly, the mitogenic effect of an HGF variant can be conveniently determined in an assay suitable for testing the ability of an HGF molecule to induce DNA synthesis of rat hepatocytes in primary cultures, such as, for example, described in Example 2. Human hepatocytes are also available from whole liver perfusion on organs deemed unacceptable for transplantation, pare-downs of adult livers used for transplantation in children, fetal livers and liver remnants removed at surgery for other indications. Human hepatocytes can be cultured similarly to the methods established for preparing primary cultures of normal rat hepatocytes. Hepatocyte DNA synthesis can, for example, be assayed by measuring incorporation of [$^3$H]thymidine into DNA, with appropriate hydroxyurea controls for replicarive synthesis.

The effect of HGF variants on hepatocyte growth can also be tested in vivo in animal models of liver dysfunction and regeneration, such as in rats following partial hepatectomy, or carbon tetrachloride caused hepatic injury, in D-galactosamine induced acute liver failure models, etc. According to a suitable protocol, a liver poison, e.g. α-naphthylisothiocyanate (ANIT) is administered to rats in a predetermined concentration capable of causing reproducible significant elevation of liver enzyme and bilirubin levels. The rats are then treated with the HGF variant to be tested, sacrificed and the liver enzyme and bilirubin levels are determined. The livers are additionally observed for hepatic lesions.

The expression "retaining substantially full receptor binding affinity of wild-type (hu)HGF" and grammatical variant thereof as used herein mean that the receptor binding affinity of the HGF variant is not less then about 70%, preferably not less than about 80%, more preferably not less than about 90%, most preferably not less than about 95% of the affinity with which wild-type (hu)HGF binds its native receptor.

The terms "substantially incapable of HGF receptor activation" and "substantially devoid of HGF biological activity" mean that the activity exhibited by an HGF variant is less than about 20%, preferably less than about 15%, more preferably less than about 10%, most preferably less than about 5% of the respective activity of wild-type (human) HGF in an established assay of receptor activation or HGF biological activity, as hereinabove defined.

The terms "amino acid" and "amino acids" refer to all naturally occurring L-α-amino acids. This definition is meant to include norleucine, ornithine, and homocysteine. The amino acids are identified by either the single-letter or three-letter designations:

| Asp | D | aspartic acid |
|-----|---|---------------|
| Thr | T | threonine |
| Ser | S | serine |
| Glu | E | glutamic acid |
| Pro | P | proline |
| Gly | G | glycine |
| Ala | A | alanine |
| Cys | C | cysteine |
| Val | V | valine |
| Met | M | methionine |
| Ile | I | isoleucine |
| Leu | L | leucine |
| Tyr | Y | tyrosine |
| Phe | F | phenylalanine |
| His | H | histidine |
| Lys | K | lysine |
| Arg | R | arginine |
| Trp | W | tryptophan |
| Gln | Q | glutamine |
| Asn | N | asparagine |

These amino acids may be classified according to the chemical composition and properties of their side chains. They are broadly classified into two groups, charged and uncharged. Each of these groups is divided into subgroups to classify the amino acids more accurately:

I. Charged Amino Acids

Acidic Residues: aspartic acid, glutamic acid
Basic Residues: lysine, arginine, histidine II. Uncharged Amino Acids Hydrophilic Residues: serine, threonine, asparagine, glutamine
Aliphatic Residues: glycine, alanine, valine, leucine, isoleucine
Non-polar Residues: cysteine, methionine, proline
Aromatic Residues: phenylalanine, tyrosine, tryptophan The terms "alteration", "amino acid alteration", "variant" and "amino acid sequence variant" refer to HGF molecules with some differences in their amino acid sequences as compared to wild-type (human) HGF. Ordinarily, the variants will possess at least about 80% homology with those domains of wild-type (human) HGF that are retained in their structure, and preferably, they will be at least about 90% homologous with such domains.

Substitutional HGF variants are those that have at least one amino acid residue in the corresponding wild-type HGF sequence removed and a different amino acid inserted in its place at the same position. The substitutions may be single, where only one amino acid in the molecule has been substituted, or they may be multiple, where two or more amino acids have been substituted in the same molecule.

Substantial changes in the activity of the HGF molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the HGF molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional HGF variants are those with one or more amino acids inserted immediately adjacent to an amino acid at a particular position in the wild-type HGF molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those with one or more amino acids in the wild-type HGF molecule removed. Ordinarily, deletional variants will have one or two amino acids deleted in a particular region of the HGF molecule.

The notations used throughout this application to describe huHGF amino acid sequence variants are described below. The location of a particular amino acid in the polypeptide chain of huHGF is identified by a number. The number refers to the amino acid position in the amino acid sequence of the mature, wild-type human HGF polypeptide as disclosed in Miyazawa et al., 1989, supra. In the present application, similarly positioned residues in huHGF variants are designated by these numbers even though the actual residue number is not so numbered due to deletions or insertions in the molecule. This will occur, for example, with site-directed deletional or insertional variants. The amino acids are identified using the one-letter code. Substituted amino acids are designated by identifying the wild-type amino acid on the left side of the number denoting the position in the polypeptide chain of that amino acid, and identifying the substituted amino acid on the right side of the number.

For example, replacement of the amino acid tyrosine (Y) by serine (S) at amino acid position 673 of the wild-type huHGF molecule yields a huHGF variant designated Y673S huHGF. Similarly, the huHGF variant obtained by substitution of serine (S) for tyrosine (Y) at amino acid position 673 and serine (S) for valine (V) at amino acid position 692 of the wild-type huHGF molecule is designated Y673S,V692S huHGF.

Deletional variants are identified by indicating the amino acid residue and position at either end of the deletion, inclusive, and placing the Greek letter delta, "Δ", to the left of the indicated amino acids. Deletion of a single amino acid is indicated by placing Δ to the left of the single letter code and number indicating the position of the deleted amino acid.

Insertional variants are designated by the use of brackets "[]" around the inserted amino acids, and the location of the insertion is denoted by indicating the position of the amino acid on either side of the insertion.

The alterations in the amino acid sequence of the HGF variants herein are indicated with reference to amino acid positions in the wild-type human HGF amino acid sequence. (Miyazawa et al., supra). Methods for the alignment of homologous amino acid sequences from various species are well known in the art.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

In the context of the present invention the expressions "cell", "cell line", and "cell culture" are used interchangeably, and all such designations include progeny.

The terms "transformed (host) cell", "transformant" and "transformed" refer to the introduction of DNA into a cell. The cell is termed a "host cell". The introduced DNA is usually in the form of a vector containing an inserted piece of DNA. The introduced DNA sequence may be from the same species as the host cell or a different species from the host cell, or it may be a hybrid DNA sequence, containing some foreign and some homologous DNA. The words transformants and transformed (host) cells include the primary subject cell and cultures derived therefrom, without regard to the number of transfers. It is also understood that all progeny may not be precisely identical in DNA content, due to deliberate or inadvertent mutations. Mutant progeny that have the same function or biological property as screened for in the originally transformed cell are included.

The technique of "polymerase chain reaction" or "PCR", as used herein, generally refers to a procedure wherein minute amounts of a specific piece of nucleic acid, RNA and/or DNA, are amplified as described in U.S. Pat. No. 4,683,195, issued 28 Jul. 1987 and in *Current Protocols in Molecular Biology,* Ausubel et al. eds., Greene Publishing Associates and Wiley-Interscience 1991, Volume 2, Chapter 15.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. The monoclonal antibodies include hybrid and recombinant antibodies produced by splicing a variable (including hypervariable) domain of an anti-selectin ligand antibody with a constant domain (e.g. "humanized" antibodies), only one of which is directed against a selectin, or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv). Cabilly, et al., U.S. Pat. No. 4,816,567; Mage & Lamoyi, in *Monoclonal Antibody Production Techniques and Applications,* pp. 79–97 (Marcel Dekker, Inc., New York, 1987). Thus, the modifier "monoclonal" indicates the character of the antibody as being obtained from such a substantially homogeneous population of antibodies, and is not to be construed as requiring production of the antibody by any particular method.

The term "immunoglobulin" generally refers to polypeptides comprising a light or heavy chain usually both disulfide bonded in the native "Y" configuration, although other linkage between them, including tetramers or aggregates thereof, is within the scope hereof.

Immunoglobulins (Ig) and certain variants thereof are known and many have been prepared in recombinant cell culture. For example, see U.S. Pat. No. 4,745,055; EP 256,654; Faulkner et al., *Nature* 298: 286 (1982); EP 120,694; EP 125,023; Morrison, *J. Immun.* 123: 793 (1979); Köhler et al., *Proc. Nat'l. Acad. Sci. USA* 77: 2197 (1980); Raso et al., *Cancer Res.* 41: 2073 (1981); Morrison et al., *Ann. Rev. Immunol.* 2: 239 (1984); Morrison, *Science* 229: 1202 (1985); Morrison et al., *Proc. Nat'l. Acad. Sci. USA* 81: 6851 (1984); EP 255,694; EP 266,663; and WO 88/03559. Reassorted immunoglobulin chains also are known. See for example U.S. Pat. No. 4,444,878; WO 88/03565; and EP 68,763 and references cited therein. The immunoglobulin moiety in the chimeras of the present invention may be obtained from IgG$_1$, IgG$_2$, IgG$_3$, or IgG$_4$ subtypes, IgA, IgE, IgD or IgM, but preferably IgG$_1$ or IgG$_3$.

II. Selection of the HGF Variants

The present invention is based upon the study of structure-activity and structure-receptor binding relationship in amino acid sequence variants of HGF.

The HGF variants of the present invention are altered at a site within the protease domain of HGF and retain substantially full receptor binding affinity of the corresponding (preferably human) wild-type HGF.

The protease domain follows the cleavage site between amino acid positions 494 and 495 in the wild-type huHGF sequence, and shows a high degree of homology with the catalytic domain of known serine proteases. The conservation does not apply to the active site of serine proteases. In human plasmin, which is formed from its proenzyme, plasminogen, residues His-42, Asp-85 and Ser-181 form the catalytic site (catalytic triad). This catalytic triad is highly conserved in serine proteases. In the huHGF amino acid sequence asparagine is retained at amino acid position 594, however, position 534 (corresponding to position 42 of plasmin) is occupied by glutamine instead of histidine, and position 673 (corresponding to position 181 of plasmin) by tyrosine instead of serine.

A preferred group of alterations herein involves one or both of amino acid positions 673 and 534. Alternatively, or in addition, the alteration may be at position 692 of the huHGF amino acid sequence. In all instances, the alteration preferably is the substitution of one or more different amino acids for the residues at these positions of the native huHGF amino acid sequence.

Tyrosine at amino acid position 673 is preferably replaced by an amino acid which has no bulky aromatic or heterocyclic moieties. Such amino acids include serine, threonine, asparagine, cysteine, glycine, alanine and valine. In the preferred variants, serine is substituted for tyrosine at this position.

Valine at amino acid position 692 preferably is substituted by a polar amino acid, such as serine, threonine, asparagine or glutamine, preferably serine.

In a preferred group of the HGF amino acid sequence variants herein, both position 673 and position 692 are substituted by one of the foregoing amino acids, preferably serine. Such variants may additionally contain an alteration (preferably substitution) at amino acid position 534. The latter alteration may be the substituion of histidine for glutamine in the wild-type huHGF amino acid sequence.

The single, double or triple mutations as hereinabove described, may be combined with additional alterations in the wild-type HGF amino acid sequence. Such further alterations may, for example, be at or around the one-chain to two chain cleavage site of the HGF molecule, and may result in variants which are substantially in single-chain form.

Absent alterations, the proteolytic cleavage takes place between Arg494 and Val495 of the wild-type huHGF sequence. The resistance to proteolytic cleavage is preferably achieved by site-directed mutagenesis within a region recognized by an enzyme capable of converting HGF into its two-chain form, and preferably within the Leu-Arg-Val-Val (LRVV) sequence at amino acid residues 493–496 of the wild-type huHGF sequence. The variants herein may, for example, contain single or multiple amino acid substitutions, insertions or deletions at or adjacent to amino acid positions 493, 494, 495 and 496 in the wild-type human HGF amino acid sequence.

A preferred alteration is the replacement of arginine at amino acid position 494 with any other amino acid, preferably glutamic acid, aspartic acid or alanine. In general, the substitution of smaller, apolar or acidic amino acids for arginine at this position is believed to yield single-chain HGF variants.

Alternatively or in addition, the replacement of valine at position 495 by another amino acid is expected to block the one-chain to two-chain cleavage. Bulkier amino acids, such as tyrosine, phenylalanine, etc. are preferred for substitution at this position.

Additional alterations may be at the C-terminal end and/or in the Kringle domains of the HGF molecule. In addition to the deletion mutants disclosed in the examples, HGF variants with alterations within the Kringle 1 domain are of great interest. As we have found that the receptor binding domain is contained within the finger and the Kringle 1 regions of the HGF molecule, amino acid alterations within these domains are expected to significantly alter the receptor binding properties (and the biological activity) of the variants of the present invention. Alterations at residues that are most exposed to the interior in the Kringle structure (mostly charged residues) are particularly likely to cause profound changes in the receptor binding properties and/or biological activity of the HGF variants.

III. Construction of the HGF Variants

Whereas any technique known in the art can be used to perform site-directed mutagenesis, e.g. as disclosed in Sambrook et al. [*Molecular Cloning: A Laboratory Manual*, second edition, Cold Spring Harbor Laboratory Press, New York (1989)], oligonucleotide-directed mutagenesis is the preferred method for preparing the HGF variants of this invention. This method, which is well known in the art [Adelman et al. *DNA*, 2: 183 (1983), Sambrook et al., Supra], is particularly suitable for making substitution variants, it may also be used to conveniently prepare deletion and insertion variants.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981). These phage are readily commercially available and their use is generally well known to those skilled in the art. Alternatively, plasmid vectors that contain a single-stranded phage origin of replication (Veira et al., *Meth. Enzymol.*, 153: 3 (1987)) may be employed to obtain single-stranded DNA.

The oligonucleotides are readily synthesized using techniques well known in the art such as that described by Crea et al. (*Proc. Nat'l. Acad. Sci. USA*, 75: 5765 [1978]).

The specific mutagenesis method followed in making the HGF variants of Example 1 was described by Kunkel et al., *Methods in Enzymol.* 154 367–382 (1987).

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

Another method for making mutations in the DNA sequence encoding wild-type HGF or a variant molecule known in the art, involves cleaving the DNA sequence encoding the starting HGF molecule at the appropriate position by digestion with restriction enzymes, recovering the properly cleaved DNA, synthesizing an oligonucleotide encoding the desired amino acid sequence and flanking regions such as polylinkers with blunt ends (or, instead of polylinkers, digesting the synthetic oligonucleotide with the restriction enzymes also used to cleave the HGF encoding DNA, thereby creating cohesive termini), and ligating the synthetic DNA into the remainder of the HGF encoding structural gene.

PCR mutagenesis is also suitable for making the HGF variants of the present invention, for example, as described in U.S. Pat. No. 4,683,195 issued 28 Jul. 1987 and in *Current Protocols in Molecular Biology*, Ausubel et al., eds. Greene Publishing Associates and Wiley-Interscience, Volume 2, Chapter 15, 1991. While the following discussion refers to DNA, it is understood that the technique also find application with RNA. The PCR technique generally refers to the following procedure. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone. If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more)-part ligation.

The cDNA encoding the HGF variants of the present invention is inserted into a replicable vector for further cloning or expression.

Suitable vectors are prepared using standard recombinant DNA procedures. Isolated plasmids and DNA fragments are cleaved, tailored, and ligated together in a specific order to generate the desired vectors.

After ligation, the vector with the foreign gene now inserted is transformed into a suitable host cell. The transformed cells are selected by growth on an antibiotic, commonly tetracycline (tet) or ampicillin (amp), to which they are rendered resistant due to the presence of tet and/or amp resistance genes on the vector. If the ligation mixture has been transformed into a eukaryotic host cell, transformed cells may be selected by the DHFR/MTX system. The transformed cells are grown in culture and the plasmid DNA (plasmid refers to the vector ligated to the foreign gene of interest) is then isolated. This plasmid DNA is then analyzed by restriction mapping and/or DNA sequencing. DNA sequencing is generally performed by either the method of Messing et al., *Nucleic Acids Res.*, 9: 309 (1981) or by the method of Maxam et al., *Methods of Enzymology*, 65: 499 (1980).

Prokaryotes are the preferred host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. For expressing the HGF variants of the present invention eukaryotic hosts, such as eukaryotic microbes (yeast) and multicellular organisms (mammalian cell cultures) may also be used. Examples of prokaryotes, e.g. *E. coli*, eukaryotic microorganisms and multicellular cell cultures, and expression vectors, suitable for use in producing the HGF variants of the present invention are, for example, those disclosed in WO 90/02798 (published 22 Mar. 1990).

Cloning and expression methodologies are well known in the art and are, for example, disclosed in the foregoing published PCT patent application (WO 90/02798).

If mammalian cells are used as host cells, transfection generally is carried out by the calcium phosphate precipitation method as described by Graham and Van der Eb, *Virology*, 52: 546 (1978). However, other methods for introducing DNA into cells such as nuclear injection, electroporation, or protoplast fusion are also suitably used.

If yeast are used as the host, transfection is generally accomplished using polyethylene glycol, as taught by Hinnen, *Proc. Natl. Acad. Sci. U.S.A.*, 75: 1929–1933 (1978).

If prokaryotic cells or cells that contain substantial cell wall constructions are used, the preferred method of transfection is calcium treatment using calcium as described by Cohen et al., *Proc. Natl. Acad. Sci. (USA)* 69: 2110 (1972), or more recently electroporation.

The HGF variant preferably is recovered from the culture medium as a secreted protein, although it also may be recovered from host cell lysates when directly expressed without a secretory signal. When the variant is expressed in a recombinant cell other than one of human origin, the variant is thus completely free of proteins of human origin. However, it is necessary to purify the variant from recombinant cell proteins in order to obtain preparations that are substantially homogeneous as to protein. As a first step, the culture medium or lysate is centrifuged to remove particulate cell debris.

The variant is then purified from contaminant soluble proteins, for example, by an appropriate combination of conventional chromatography methods, e.g. gel filtration, ion-exchange, hydrophobic interaction, affinity, immunoaffinity chromatography, reverse phase HPLC; precipitation, e.g. ethanol precipitation, ammonium sulfate precipitation, or, preferably, immunoprecipitation with anti-HGF (polyclonal or monoclonal) antibodies covalently linked to Sepharose. Due to its high affinity to heparine, HGF can be conveniently purified on a heparin, such as heparine-Sepharose column. One skilled in the art will appreciate that purification methods suitable for native HGF may require modification to account for changes in the character of HGF or its variants upon expression in recombinant cell culture.

As hereinabove described, huHGF contains four putative glycosylation sites, which are located at positions 294 and 402 of the α-chain and at positions 566 and 653 of the β-chain. These positions are conserved in the rat HGF amino acid sequence. Glycosylation variants are within the scope herein.

Glycosylation of polypeptides is typically either N-linked or O-linked. N-linked refers to the attachment of the carbohydrate moiety to the side-chain of an asparagine residue. The tripepride sequences, asparagine-X-serine and asparagine-X-threonine, wherein X is any amino acid except proline, are recognition sequences for enzymatic attachment of the carbohydrate moiety to the asparagine side chain. O-linked glycosylation refers to the attachment of one of the sugars N-acetylgalactosamine, galactose, or xylose to a hydroxyamino acid, most commonly serine or threonine, although 5- hydroxyproline or 5-hydroxylysine may also be involved in O-linked glycosylation. O-linked glycoslation sites may, for example, be modified by the addition of, or substitution by, one or more serine or threonine residue to the amino acid sequence of the HGF molecule. For ease, changes are usually made at the DNA level, essentially using the techniques discussed hereinabove with respect to the amino acid sequence variants.

Chemical or enzymatic coupling of glycosydes to the HGF variants of the present invention may also be used to modify or increase the number or profile of carbohydrate substituents. These procedures are advantageous in that they do not require production of the polypeptide that is capable of O-linked (or N-linked) glycosylation. Depending on the coupling mode used, the sugar(s) may be attached to (a) arginine and histidine, (b) free carboxyl groups, (c) free hydroxyl groups such as those of cysteine, (d) free sulfhydryl groups such as those of serine, threonine, or hydroxyproline, (e) aromatic residues such as those of phenylalanine, tyrosine, or tryptophan or (f) the amide group of glutamine. These methods are described in WO 87/05330 (published 11 Sep. 1987), and in Aplin and Wriston, *CRC Crit. Rev. Biochem.*, pp. 259–306 ( 1981).

Carbohydrate moieties present on an HGF variant may also be removed chemically or enzymatically. Chemical deglycosylation requires exposure to trifluoromethanesulfonic acid or an equivalent compound. This treatment results in the cleavage of most or all sugars, except the linking sugar, while leaving the polypeptide intact. Chemical deglycosylation is described by Hakimuddin et al., *Arch. Biochem. Biophys.* 259, 52 (1987) and by Edge et al., *Anal. Biochem.* 118, 131 (1981). Carbohydrate moieties can be removed by a variety of endo- and exoglycosidases as described by Thotakura et al., *Meth. Enzymol.* 138, 350 (1987). Glycosylation is suppressed by tunicamycin as described by Duskin et al., *J. Biol. Chem.* 257, 3105 (1982). Tunicamycin blocks the formation of protein-N-glycosydase linkages.

Glycosylation variants of the amino acid sequence variants herein can also be produced by selecting appropriate host cells. Yeast, for example, introduce glycosylation which varies significantly from that of mammalian systems. Similarly, mammalian cells having a different species (e.g. hamster, murine, insect, porcine, bovine or ovine) or tissue (e.g. lung, liver, lymphoid, mesenchymal or epidermal) origin than the source of the selectin variant, are routinely screened for the ability to introduce variant glycosylation.

Covalent modifications of an HGF variant molecule are included within the scope herein. Such modifications are traditionally introduced by reacting targeted amino acid residues of the HGF variant with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays of the HGF variants, or for the preparation of anti-HGF antibodies for immunoaffinity purification of the recombinant glycoprotein. For example, complete inactivation of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Derivatization with bifunctional agents is useful for preparing intramolecular aggregates of the HGF variants as well as for cross-linking the HGF variants to a water insoluble support matrix or surface for use in assays or affinity purification. In addition, a study of interchain cross-links will provide direct information on conformational structure. Commonly used cross-linking agents include 1,1-bis(diazoacetyl)-2-phenylethane, glutaraldehyde, N-hydroxysuccinimide esters, homobifunctional imidoesters, and bifunctional maleimides. Derivatizing agents such as methyl-3-[(p-azidophenyl)-dithio]propioimidate yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

Other derivatives comprise the novel HGF variants of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The HGF variants may be linked to various nonproteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337.

The HGF variants may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remington's Pharmaceutical Sciences*, 16th Edition, Osol, A., Ed. (1980).

An HGF variant sequence can be linked to a immunoglobulin constant domain sequence as hereinbefore defined. The resultant molecules are commonly referred to as HGF variant-immunoglobulin chimeras.

Such chimeras can be constructed essentially as described in WO 91/08298 (published 13 Jun. 1991).

Ordinarily, the HGF variant is fused C-terminally to the N-terminus of the constant region of an immunoglobulin in place of the variable region(s), however N-terminal fusions of the selectin variants are also desirable. The transmembrane regions of the HGF variants are preferably inactivated or deleted prior to fusion.

Typically, such fusions retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. This ordinarily is accomplished by constructing the appropriate DNA sequence and expressing it in recombinant cell culture. Alternatively, however, the HGF variant-immunoglobulin chimeras of this invention may be synthesized according to known methods.

The precise site at which the fusion is made is not critical; particular sites are well known and may be selected in order to optimize the biological activity, secretion or binding characteristics of the HGF variant.

In some embodiments, the hybrid immunoglobulins are assembled as monomers, or hetero- or homo-multimers, and particularly as dimers of tetramers, essentially as illustrated in WO 91/08298, Supra.

In a preferred embodiment, the C-terminus of a sequence which contains the binding site(s) for an HGF receptor, is fused to the N-terminus of the C-terminal portion of an antibody (in particular the Fc domain), containing the effector functions of an immunoglobulin, e.g. immunoglobulin $G_1$. It is possible to fuse the entire heavy chain constant region to the sequence containing the receptor binding site(s). However, more preferably, a sequence beginning in the hinge region just upstream of the papain cleavage site (which defines IgG Fc chemically; residue 216, taking the first residue of heavy chain constant region to be 114 [Kobet et al., Supra], or analogous sites of other immunoglobulins) is used in the fusion. In a particularly preferred embodiment, the amino acid sequence containing the receptor binding site(s) is fused to the hinge region and $C_H2$ and $C_H3$ or $C_H1$, hinge, $C_H2$ and $C_H3$ domains of an $IgG_1$, $IgG_2$ or $IgG_3$ heavy chain. The precise site at which the fusion is made is not critical, and the optimal site can be determined by routine experimentation.

HGF variant-immunoglobulin chimeras may, for example, be used in protein A purification, immunohistochemistry, and immunoprecipitation techniques in place of anti-HGF antibodies, and can facilitate screening of inhibitors of HGF-HGF receptor interactions. Therapeutically, they are expected to confer advantages such as longer half-life as compared to the corresponding HGF variant molecule.

IV. Therapeutic Compositions

The HGF variants with enhanced receptor binding affinity can be used to block the binding of wild-type HGF to its receptor. This would permit the treatment of pathologic conditions associated with the activation of an HGF receptor, such as malignancies associated with chronic HGF receptor activation.

The compounds of the present invention can be formulated according to known methods to prepare pharmaceutically useful compositions, whereby the HGF product is combined in admixture with a pharmaceutically acceptable carrier. Suitable carriers and their formulations are described in *Remington's Pharmaceutical Sciences*, 16th ed., 1980, Mack Publishing Co., edited by Oslo et al., specifically incorporated by reference. These compositions will typically contain an effective amount of the HGF variant, for example, from on the order of about 0.5 to about 10 mg/ml, together with a suitable amount of carrier to prepare pharmaceutically acceptable compositions suitable for effective administration to the patient. The variants may be administered parenterally or by other methods that ensure its delivery to the bloodstream in an effective form.

Compositions particularly well suited for the clinical administration of the HGF variants used to practice this invention include sterile aqueous solutions or sterile hydratable powders such as lyophilized protein. Typically, an appropriate amount of a pharmaceutically acceptable salt is also used in the formulation to render the formulation isotonic.

Dosages and desired drug concentrations of pharmaceutical compositions of this invention may vary depending on the particular use envisioned. A typical effective dose in rat experiments is about 250 $\mu g/kg$ administered as an intravenous bolus injection. Interspecies scaling of dosages can be performed in a manner known in the art, e.g. as disclosed in Mordenti et al., *Pharmaceut. Res.* 8, 1351 (1991) and in the references cited therein.

The following examples merely illustrate the best mode now contemplated for practicing the invention, but should not be construed to limit the invention.

Examples

A series of recombinant huHGF (rhuHGF) variants were produced to determine the structural and functional importance of the cleavage of the prohormone to the $\alpha/\beta$ dimer and of the Kringle and protease-like domains. Mutations were introduced into the huHGF cDNA in a CMV based expression plasmid and conditioned media from stable populations of human 293 cells expressing each variant were assayed by Western blotting to monitor the size and expression level of the HGF variants.

The concentration of each huHGF derivative was confirmed with two types of sandwich ELISA assays. The differences in expression levels found in ELISA correlated with those observed on Western blots. For most variants, the level of expression was in the range of 1-5 mg/mL. For variants with expression levels below 0.6 mg/mL, the conditioned media was concentrated.

The mitogenic activity on liver cells in primary culture and ability to bind to the HGF receptor was then determined. The extra-cellular domain of the HGF receptor was fused to the constant region (Fc) of an human IgG and binding was performed in solution.

The construction of the rhuHGF variants, the assay methods and the analysis of the results obtained with the various mutants are described in the following examples.

EXAMPLE 1

Recombinant Production of the huHGF Variants

A. Site-Directed Mutagenesis

Plasmid DNA isolation, polyacrylamide and agarose gel electrophoresis were performed as disclosed in Sambrook et al., supra.

Mammalian expression plasmid pRK 5.1 with a CMV promotor (Genentech, Inc.) was used for mutagenesis of huHGF allowing secretion of the HGF variants in the culture medium and directly assayed for biological activity and binding. This expression vector is a derivative of pRK5, the construction of which is disclosed in EP 307,247 published 15 Mar. 1989. The nucleotide of all four deoxyribonucleotide triphosphates, ATP, and DNA ligase.

The following oligonucleotides were prepared to use as primers to generate pRK 5.1-huHGF variant molecules:

| R494E huHGF: | TTGGAATCCCATTTACAACCTCGAGTTGTTTCGTTTTGGCACAAGAT | (SEQ. ID. NO: 2) |
| --- | --- | --- |
| R494D huHGF: | GAATCCCATTTACGACGTCCAATTGTTTCG | (SEQ. ID. NO: 3) |
| R494A huHGF: | CCCATTTACAACTGCCAATTGTTTCG | (SEQ. ID. NO: 4) |
| Q534H huHGF: | AGAAGGGAAACAGTGTCGTGCA | (SEQ. ID. NO: 5) |
| Y673S huHGF: | AGTGGGCCACCAGAATCCCCCT | (SEQ. ID. NO: 6) |
| V692S huHGF: | TCCACGACCAGGAGAAATGACAC | (SEQ. ID. NO: 7) |
| ΔK1 huHGF: | GCATTCAACTTCTGAGTTTCTAATGTAGTC | (SEQ. ID. NO: 8) |
| ΔK2 huHGF: | CATAGTATTGTCAGCTTCAACTTCTGAACA | (SEQ. ID. NO: 9) |
| ΔK3 huHGF: | TCCATGTGACATATCTTCAGTTGTTTCCAA | (SEQ. ID. NO: 10) |
| ΔK4 huHGF: | TGTGGTATCACCTTCATCTTGTCCATGTGA | (SEQ. ID. NO: 11) |
| N-303 huHGF: | ACCTTGGATGCATTAAGTTGTTTC | (SEQ. ID. NO: 12) |
| N-384 huHGF: | TTGTCCATGTGATTAATCACAGT | (SEQ. ID. NO: 13) |
| α-chain: | GTTCGTGTTGGGATCCCATTTACCTATCGCAATTG | (SEQ. ID. NO: 14) | sequence encoding this the pRK 5.1 vector is shown in FIG. 5 (SEQ. ID. NO: 1).

The huHGF cDNA used corresponds to the 728 amino acid form as published earlier (Miyazawa et al., 1989, supra).

Mutagenesis was performed according to the method of Kunkel using the commercially available dut- ung- strain of E. coli [Kunkel et al., Method. Enzymol. 154, 367–382 (1987)]. Synthetic oligonucleotides used for in vitro mutagenesis and sequencing primers were prepared using the Applied Biosystem 380A DNA synthesizer as described [Matteucci et al., J. Am. Chem. Soc. 103, 3185–3191 (1981)]. For generation of the desired mutants, oligonucleotides of sequences coding for the desired amino acid substitutions were synthesized and used as primers. The oligonucleotides were annealed to single-stranded pRK51-huHSA that had been prepared by standard procedures [Viera et al., Method. Enzymol. 142, 3 (1987)].

A mixture of three deoxyribonucleotides, deoxyriboadenosine (dATP), deoxyriboguanosine (dGTP), and deoxyribothymidine (dTTP), was combined with a modified thio-deoxyribonuleosine called dCTP(aS) provided in the kit by the manufacturer, and added to the single stranded pRK 5.1-huHGF to which was annealed the oligonucleotide.

Upon addition of DNA polymerase to this mixture, a strand of DNA identical to pRK 5.1-huHGF except for the mutated bases was generated. In addition, this new strand of DNA contained dCTP(aS) instead of dCTP, which served to protect from restriction endonuclease digestion. After the template strand of the double-stranded heteroduplex was nicked with an appropriate restriction enzyme, the template strand was digested with ExoIII nuclease past the region that contained the mutagenic oligomer. The reaction was then stopped to leave a molecule hat was only partly single-stranded. A complete double-stranded DNA homoduplex molecule was then formed by DNA polymerase in the presence The Y673S, V692S huHGF variant was obtained from wild-type huHGF as a template, using both oligonucleotides used for generating the two mutations.

The mutant huHGF constructs generated using the protocol above were transformed in E. coli host strain MM294tonA using the standard calcium chloride procedure (Sambrook et al., supra) for preparation and transformation of competent cells. MM294tonA (which is resistant to T1 phage) was prepared by the insertion and subsequent imprecise excision of a Tn10 transposon into the tonA gene. This gene was then inserted, using transposon insertion mutagenesis [Kleckner et al., J. Mol. Biol. 116, 125–159 (1977)], into E. coli host MM294 (ATCC 31,446).

The DNA extract from individual colonies of bacterial transformants using the standard miniprep procedure of Sambrook et al., supra. The plasmids were further purified by passage over a Sephacryl CL6B spin column, and then analyzed by sequencing and by restriction endonuclease digestion and agarose gel electrophoresis.

B. Transfection of Human Embryonic Kidney 293 Cells

Plasmids with the correct sequence were used to transfect human fetal kidney 293 cells by the calcium phosphate method. 293 cells were growth to 70% confluence in 6-well plates. 2.5 µg of huHGF plasmid DNA variant was dissolved in 150 µl of 1 mMTris-HCl, 0.1 mM EDTA, 0,227 M CaCl₂. Added to this (dropwise while vortexing) was 150 µl of 50 mMHEPES buffer (pH 7.35), 280 mM NaCl, 1.5 mM NAPO₄, and the precipitate was allowed to form for ten minutes at 25° C. The suspended precipitate was then added to the cells in the individual wells in a 6-well plate. The cell monolayers were incubated for 4 hours in the presence of the DNA precipitate, washed once with PBS, and cultured in serum-free medium for 72 h. When stable populations were made, the HGF cDNA was subcloned in an episomal CMV driven expression plasmid pCisEBON (G. Cachianes, C, Ho, R. Weber, S. Williams, D. Goeddel, and D. Lueng, in preparation). pCisEBON is a pRK5 derivative; its underlying nucleotide sequence is shown in FIG. 6 (SEQ. ID. NO: 15). The populations were directly selected in Neomycin selective medium.

EXAMPLE 2

Assay Methods

In view of the pleiotropic activities of HGF, a molecule with a structure unlike any other known growth factor, it is important to understand the molecular interaction of this factor with its receptor. The huHGF variants produced as described in Example 1 were analyzed for their ability to induce DNA synthesis of hepatocytes in primary culture and to compete for binding to a soluble form of the huHGF receptor.

A. Protein Quantification of Wild-Type huHGF and huHGF Variants

A specific two-site huHGF sandwich ELISA using two monoclonal antibodies was used to quantify wild-type recombinant huHGF (WT rhuHGF), single chain and protease substitution variants. Microtiter plates (Maxisorb, Nunc) were coated with 10 mg/ml of a monoclonal anti-rhuHGF antibody A 3.1.2 (IgG2a phenotype, affinity: $3.2 \times 10^{-8}$ mol) in 50 mM Carbonate buffer, pH 9.6, overnight at 4° C. After blocking plates with 0.5% BSA (Sigma), 0.01% thimerosal in PBS, pH 7.4, and subsequent washes, duplicate serial dilutions of HGF samples were prepared and in parallel a CHO-expressed rhuHGF (40-0.1 ng/mL) was used as a standard. Fifty microliters of these dilutions were simultaneously incubated with 50 mL of a 1:1500 diluted horseradish peroxidase conjugated monoclonal anti-rhuHGF antibody B 4.3 (IgG1 phenotype, affinity: $1.3 \times 10^{-8}$ mol) for 2 h at RT. The substrate was prepared by adding 0.04% o-phenylenediamine-dihydrochloride (Sigma) and 0,012% (v/v) hydrogen-peroxide (Sigma) to PBS and 100 ml were added to the washed plates for 15 minutes at RT. The reaction was stopped by adding 50 mL of 2.25M sulfuric acid to each well. The absorbance at 490 nm, with the absorbance at 405 nm subtracted as background, was determined on a microtiter plate reader (Vmax, Molecular Devices, Menlo Park, Calif.). The data was reduced using a four-parameter curve-fitting program developed at Genentech, Inc.

An HGF polyclonal sandwich ELISA was used to quantify all kringle deletion and C-terminal truncation variants. Briefly, microtiter plates (Nunc) were coated with 5 mg/mL guinea pig polyclonal (anti CHO-expressed rhuHGF) IgG antibody preparation (Genentech, Inc.) as described above. This antibody recognizes rhuHGF as well as HGF truncated forms when compared to visual inspection of Western blots, making it ideal for monitoring HGF variants. Plates were blocked and duplicate serial dilutions of 293 cell supernatants (1:103-6.106) were added and incubated over night at 4° C. Purified CHO-expressed rhuHGF (100-0.78 ng/mL) was used as a standard and incubated in parallel. Plates were washed and incubated with a 1:500 dilution of the same polyclonal antibody (approx. 400 ng/mL) but in this case horseradish peroxidase conjugated for detection of the variants (see above). Western blotting was performed to determine the size of the expressed HGF variants. For this, SDS-polyacrylamide gel electrophoresis and Western blotting were performed using standard methods with the polyclonal IgG antibody preparation (500 ng/mL). A chemiluminescent detection method (Amersham) and a goat anti-guinea pig IgG-horseradish peroxidase conjugate (1:5000) were used for development of the blot as described by the manufacturer.

B. Soluble HGF Receptor Binding Assay

Previous studies on HGF binding to hepatocytes have shown that huHGF could bind to its cell surface receptor with high affinity (Kd~24–32 pM; Higuchi and Nakamura, *Biochem. Biophys. Res. Comm.* 174, 831-838 (1991)). We preferred to examine HGF binding using a soluble form of the receptor because of the nonspecific binding of HGF to cell surface heparin sulfate proteoglycans [Naldini et al., *EMBO J.* 10, 2867-2878 (1991)].

Cell supernatants (concentrated on Amicon filters if concentration was below 600 ng/mL) were tested for their ability to block in solution the binding of CHO-expressed $^{125}$I rhuHGF ($2-5 \times 10^3$ Ci/mmole, kindly provided by T. Zioncheck, Genentech, Inc.) to the extracellular domain of the human HGF receptor (huHGFr) fused to the Fc constant region of an human IgG, expressed and secreted from 293 cells.

1. Construction of huHGFr-IgG chimeras

A full length cDNA clone encoding the huHGFr was constructed by joining partial cDNAs isolated from cDNA libraries and from PCR amplification. Coding sequences for amino acids 1–270 were isolated from a human placental cDNA library (provided by T. Mason, Genentech) screened with a 50 mer oligonucleotide (5'-ATGAAGGCCCCCGCTGTGCTTGCACCTG-GCATCCTCGTGCTCCTGTTTACC-3') (SEQ. ID. NO: 16). Sequences encoding amino acids 809–1390 were isolated from a human liver library (Stragagen) screened with the oligonucleotide probe (5'-CAC-TAGTTAGGATGGGGGACATGTCTGT-CAGAGGATACTGCACTTGTCGGCAT-GAACCGT-3'). (SEQ. ID. NO: 17)

Conditions for plating libraries, and for hybridization and washing filters were as described [Godowski et al., *Proc. Natl. Acad. Sci. USA* 86, 8083–8087 (1989)]. PCR was used to isolate a cDNA clone containing residues 271–808 of the HGFr (c-met) from A549 cells. Ten μgs of total RNA was used for reverse transcription using a primer specific to the HGFr (5'-TAGTACTAGCAC-TATGATGTCT-3') (SEQ. ID. NO: 18) in a 100 μl reaction using Moloney murine leukemia virus reverse transcriptase and buffers supplied by Bethesda Research Laboratories. One-tenth of this reaction mixture was used for PCR amplification. The PCR reaction was performed in a volume of 100 μl containing 10 μl of the reverse transcriptase reaction, 10 mM KCl, 20 mMTris-HCl (pH 8.8), 10 mM (NH4)SO4, 6 mM MgSO4, 0.1% Trition X-100, 1 U of Vent DNA polymerase (New England Biolabs) and 50 pmol each of the forward primer (5'-TTTACTTCTTGACGGTCCAAAG-3' (SEQ. ID. NO: 19) and the reverse primer (5'-CAGGGGGAGTTGCAGATTCAGCTGT-3') (SEQ. ID. NO: 20). After thirty cycles of denaturation (95° C., 1 min), annealing (55° C., 45 secs) and extension (72° C., 2 min), the PCR product were recovered from low-melting temperature agarose gels. The full-length HGFr cDNA was subcloned into vector pRK7 (see WO 90/02798, published 22 Mar. 1990) and double-stranded DNA sequencing was performed by the dideoxynucleotide method.

The coding sequence of the extracellular domain of the huHGFr was fused to those of the human IgG1 heavy chain in a two-step process. PCR was used to generate a fragment with a unique BstEII site 3' to the coding sequences of the HGFr amino acid 929. The 5' primer (located in the vector upstream of the HGFr coding sequences) and the 3' primer (5'-AGTTTTGTCGGTGACCTGATCATTCT-GATCTGGTTGAACTATTAC-3') (SEQ. ID. NO: 21) were used in a 100 µl reaction as described above except that the extension time at 72° C. was 3 minutes, and 40 ng of the full length HGFr expression vector was used as template. Following amplification, the PCR product was joined to the human IgG-γ1 heavy chain cDNA through a unique BstEII site in that construct [Bennett et al., *J. Biol. Chem.* 266, 23060–23067 (1991)]. The resulting construct contained the coding sequences of amino acids 1-929 of the huHGFr fused via the BstEII site (adding the coding sequences for amino acids V and T) to the coding sequences of amino acids 216–443 of the human IgG-γ1 heavy chain. Sequencing of the construct was carried out as described above.

2. Binding assay

The binding assay was performed in breakable microtiter plates (Nunc) coated o/n at 4° C. with 1 mg/mL of rabbit-anti-human IgG Fc specific antibody (Jackson Immunoresearch) and plates were carefully washed with PBS containing 0.05% Tween 20 (Biorad). After blocking with PBS containing 0.1% BSA, in this same buffer, 50pM of 125I-rhuHGF in 25 mL per well were added. To each well 50 mL of serial dilutions (1:25–1:6000) of cell supernatants, purified CHO-expressed rhuHGF (25,000–0.064 pM) or medium were added in duplicates. Subsequently, 25 mL of 50 pM of HGF receptor:IgG fusion protein were added and the plates were incubated with gentle shaking. After 4 hours, when equilibrium was reached, plates were washed and wells were individually counted in a gamma-counter. The amount of nonspecifically bound radioactivity was estimated by incubating HGF receptor:IgG with a 500-fold excess of unlabelled rhuHGF. The dissociation constant (Kd) of each analogue was calculated at the IC50 from fitted inhibition curves essentially as described (DeBlasi et al., 1989 [?]) using the huHGF concentration determined by ELISA.

C. Biological Assay

The biological activity of WT huHGF and variants was measured by their abilities to induce DNA synthesis of rat hepatocytes in primary culture. Hepatocytes were isolated according to published perfusion techniques with minor modifications [Garrison and Haynes, *J. Biol. Chem.*, 150, 2269–277 (1975)]. Briefly, the livers of female Sprague Dawley rats (160–180 g) were perfused through the portal vein with 100 mL of $Ca^{++}$ free Hepes buffered saline containing 0.02% Collagenase type IV (Sigma). After 20 minutes the liver was removed, placed in buffer, gently stirred to separate hepatocytes from connective tissue and blood vessels, and filtered through nylon mesh. Cells were then washed by centrifugation, resuspended at $1 \times 10^5$ cells/mL in Williams Media E (Gibco) containing Penicillin (100 U/ml), Streptomycin (100 mg/mL), L-Glutamine (2 mM), trace elements (0.01%), transferrin (10 mg/mL) and Aprotinin (1 mg/mL). Hepatocytes were incubated in 96-well microtiter plates (Falcon) in the presence of duplicate serial dilutions of either purified CHO-expressed rhuHGF (1–0.031 mg/mL), 293 supernatants (1:4–1:256) or medium. After 48 hours incubation at 37° C., 0.5 mCi 3H-TdR (15 Ci/mmole, Amersham) was added to each well and incubated for an additional 16 hours. Cells were harvested on filter papers, which were washed, dried and counted in a Beckman counter after addition of scintillation liquid. For each huHGF variant, the specific activity (SA) expressed in units/mg was calculated at half-maximal proliferation (defined as 1 unit/mL) using the HGF concentration obtained in ELISA.

D. Induction of Tyrosine Phosphorylations on A549 Cells

Human lung carcinoma cells (A549) monolayers were cultured in RPMI 1640 medium containing 10% fetal bovine serum and maintained at 37° C. in a humidified atmosphere with 5% $CO_2$. Serum-starved cells were incubated without or with 200 ng/mL rhuHGF for 5 minutes at 37° C. and extracted with lysis buffer containing 50mM Hepes, 150 mM NaCl, 1.5 mM $MgCl_2$, 1 mM EGTA, 10% Glycerol, 1% Triton X-100 and a cocktail of protease inhibitors. The lysates were immunoprecipitated with anti-Met COOH antibodies and blotted with anti-phosphotyrosine antibodies (see Western blotting above).

EXAMPLE 3

Analysis of Cleavage Site Mutants

Figure 2:
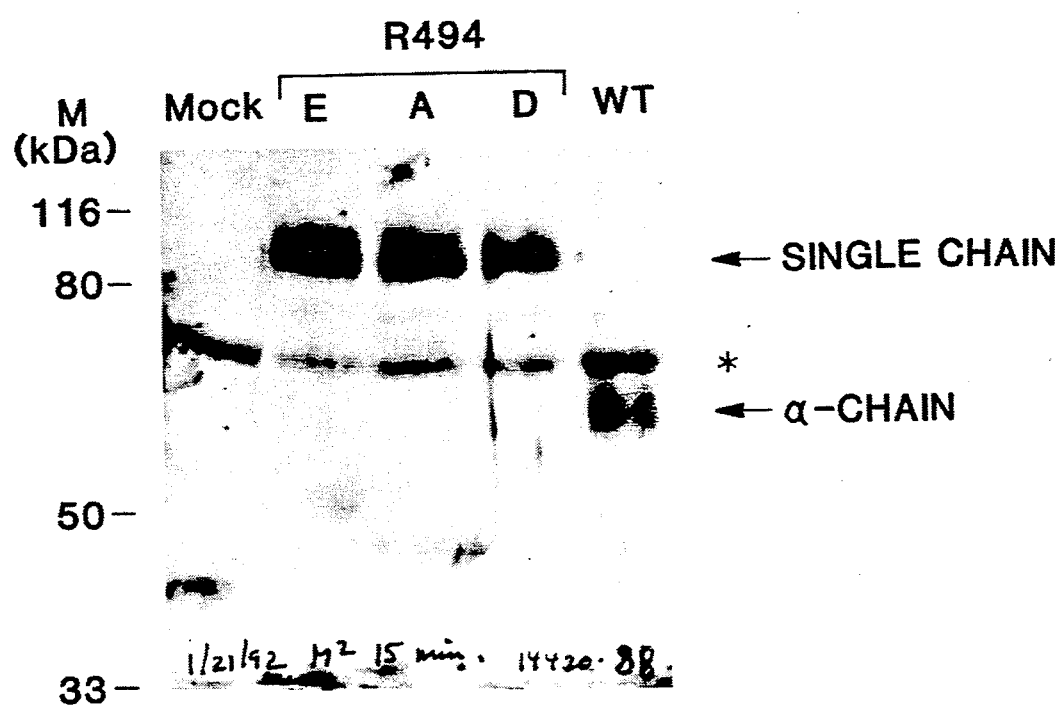
FIG. 2 shows the results of Western blot of wild-type rhuHGF and single-chain variants. Conditioned media from mock transfected 293 cells or stable 293 cells expressing either wild-type rhuHGF (WT) or the variants R494E, R494A or R494D were fractionated under reducing conditions on an 8% sodium-dodecyl sulfate-polyacrylamide gel and blotted. The blot was reacted with polyclonal anti-HGF antisera which recognizes epitopes primarily in the α-chain. Molecular masses (kilodaltons) of the marker are as indicated. Also indicated are the positions of the α-chain and uncleaved single-chain forms of huHGF. Note that the polyclonal antibody cross-reacts with an unidentified band (*) present even in the control transfected 293 cells, which do not express detectable quantities of huHGF.
Figure 3A:
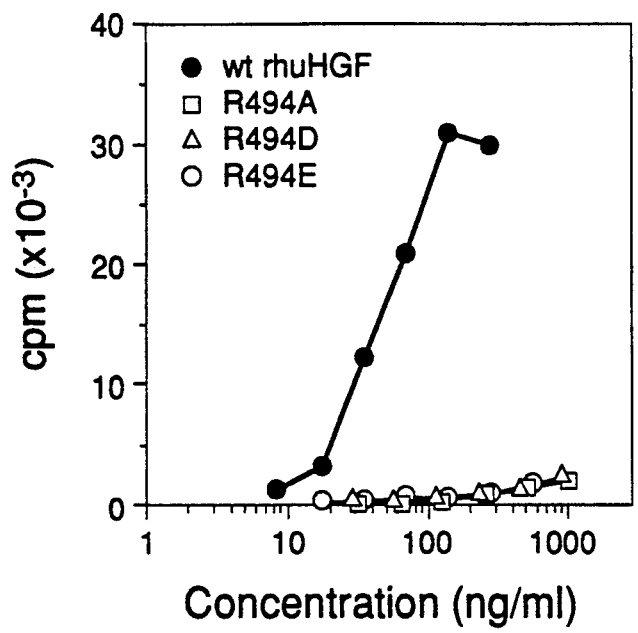
FIGS. 3A and 3B: Mitogenic activity (A) and competitive receptor binding (B) of wild-type (WT) rhuHGF and single-chain variants. (A) Biological activity was determined by the ability of WT rhuHGF and variants to induce DNA synthesis of rat hepatocytes in primary culture as described in Example 2. Shown are the mean cpm from duplicates in a representative assay. Mock supernatant from control cells did not stimulate DNA synthesis in these cells (no cpm increase above background levels). (B) To perform competitive binding, various dilutions of supernatants of human 293 cells containing wt rhuHGF or variants were incubated with 50 pM of the huHGF receptor-IgG fusion protein as described in Example 2. Data represent inhibition of binding as the percentage of any competing ligand from a representative experiment and were corrected by subtraction of background values from control 293 cells.
Figure 3B:
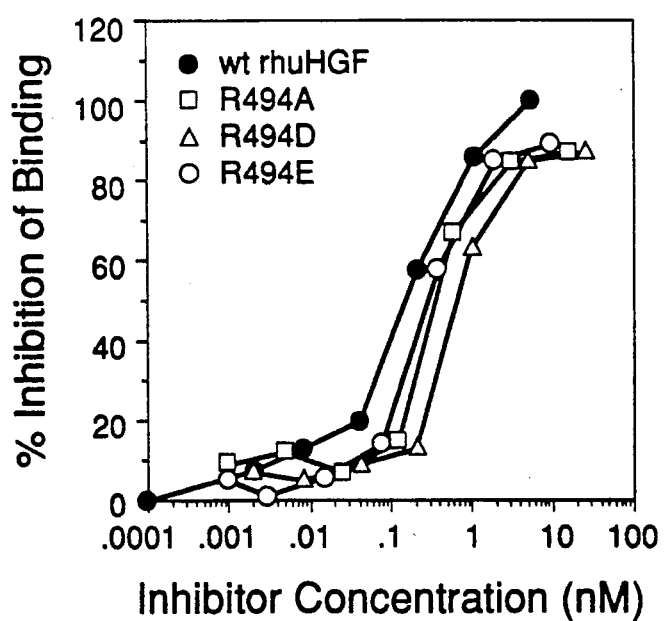

The cleavage site of proteases commonly contains a basic residue at position P1 and two hydrophobic amino acid resides in positions P'1 and P'2, which follow the cleaved peptide bond. The proposed cleavage site of huHGF (P1 R494, P'1 V495, P'2 V496) fits this consensus. We chose to try to block cleavage of huHGF by replacing the P1 R494 with either D, E, or A. The major form of WT rhuHGF expressed in these cells is cleaved into two-chain material as judged by the presence of the α-chain with an apparent molecular mass of 69 kDa (FIG. 2). Each of these mutations appeared to block processing of rhuHGF because under reducing conditions these variants migrated as a single band at 94 kDa, the predicted size of single-chain HGF. These variants totally lacked the ability to induce the proliferation of hepatocytes in primary culture (FIG. 3A). However, when these variants were analyzed for their ability to compete with WT rhuHGF for binding to the HGF receptor:IgG fusion protein, their inhibition curves were roughly similar to that of WT rhuHGF (FIG. 3B). The Kd determined from these curves showed that WT rhuHGF binds to the fusion protein with high affinity (50–70 pM) whereas all single chain variants showed approximately a 2- to 10-fold higher Kd (100–500 pM) compared to WT rhuHGF. Results from at least three independent assays are summarized in Table I as residual hepatocyte proliferative activity and receptor binding capacity compared to WT rhuHGF.

Our binding studies showed that WT rhuHGF bound to the soluble receptor fusion protein with a single class of high affinity binding sites (50–70 pM), similar to those found on hepatocytes by Higushi and Makamura (1991). However, binding of HGF on cells may slightly be different since the soluble receptor is actually a dimer held together by the disulfide bridge of the hinge in the Fc portion of the IgGA.

Direct comparison of specific activity (SA) versus Kd ratios of all single chain variants showed they were inactive at the highest concentration tested (SA>3%) while receptor binding affinities were only decreased by a factor of 2-3.

These results argue strongly that cleavage of HGF into the two-chain form is required for mitogenic activity, i.e. that single-chain HGF is a promitogen and that the uncleaved form of HGF binds to the HGF receptor, albeit with a reduced affinity.

The major form of HGF isolated from placenta [Hernandez et al., (1992) *J. Cell Physiol.*, in press] or expressed in transfected COS cells [Rubin et al., *Proc. Natl. Acad. Sci. USA* 88, 415-419 (1991)] is in single-chain form. When tested in mitogenic assays, this single-chain form of HGF is found to be biologically active. Taken together with our data, this suggests that this single-chain HGF is activated to the two-chain form during the mitogenic assay.

A second observation is that single-chain variants retain substantial capacity to bind to the HGF receptor, as suggested by our competition binding assays. This raises the interesting possibility that single-chain HGF may be bound to cell-surface HGF receptor in vivo in an inactive state and can subsequently be cleaved to the active double-chain form by the appropriate protease.

EXAMPLE 4

The Effects of Protease Domain Mutations

To elucidate the functional importance of the protease domain of HGF, several single, double and triple mutations were made in order to reconstitute a potential serine-protease active site. The construction of these variants is described in Example 1.

We replaced HGF residues Q534 with H, Y673 with S, or V692 with S as either single, double or triple mutations. The analysis of their effects on mitogenic activity and receptor binding showed that the single mutation Q534H did not significantly alter either SA ($5.2 \times 10^4$ Units/mg) or Kd (60 pM) when compared to wt rhuHGF (respectively 3.3 $10^4$ Units/mg and 70 pM) whereas Y673S and V692S exhibited SA reduced approximately 5- and 10-fold, respectively. In fact, these two variants never reached the maximum plateau seen with WT rhuHGF (approximately 50% of wt rhuHGF plateau). Interestingly, these variants showed a Kd similar to WT rhuHGF. All other double and triple variants also retained the ability to bind the HGF receptor but they clearly showed a reduced SA (Table I). The residual SA of the double variants Q534H,Y673S and Y673S,V692S and of the triple variant Q534H,Y673S,V692S were less than 3% compared to WT rhuHGF. However, the Kd of these variants was not significantly different from WT rhuHGF (Table I). These variants indicate that mutations within the β-chain of HGF block mitogenic activity but they are still able to bind to the HGF receptor. Thus, it appears that these mutants are defective in an activity subsequent to receptor binding.

These results show that although the β-chain is not required for receptor binding, certain residues (e.g. Y673 and V692) are critical for the structure and/or activity of HGF. Substitution of the nonpolar residue V692 with the polar residue S might have caused a structural transition if new hydrogen bonds to the active site residue D594, as found in serine-proteases, have been introduced. Substitution of Y673 with the smaller residue S might also introduce some local structural modifications. On the other hand, replacement of the polar residue Q534 by another polar residue H of similar size would not likely cause a drastic difference in the HGF conformation as this residue should be exposed; indeed the Q534H variant was similar to rhuHGF (Table I).

EXAMPLE 5

The Effect of C-terminal and Kringle Deletions

In order to ascertain whether the α-chain is required for HGF binding or activity, C-terminal truncations were made as described in Example 1, resulting in variants containing either the α-chain alone, or variants truncated after the third (N-384) or second (N-303) Kringles.

A number of C-terminal truncations of HGF were made by deleting either the β-chain or the β-chain in addition to a progressive number of kringles as depicted in FIG. 1. One variant (N-207) corresponding to the N-terminal domain with the first Kringle did not express the protein to levels detectable either by Western blotting or ELISA using a polyclonal antibody preparation and thus was not investigated further. Expression of the variants containing the first two Kringles (N-303), three Kringles (N-384) or the complete α-chain of HGF was as low as 250-600 ng/mL. A summary of the residual SA and Kd compared to WT rhuHGF of these variants is presented in Table I. At the concentration tested no activity above background levels was observed indicating that these variants lost their biological activity. However, binding competition showed that variants N-303, N-384 or the α-chain still retained substantial binding capacity (up to 23% compared to WT rhuHGF binding). Thus, the N-terminal 272 residues of HGF (the mature form of variant N-303) are sufficient for high affinity binding to the HGF receptor.

Results from deleting each kringle domain are shown in Table I. Deletion of the first Kringle (variant ΔK1) of HGF affected biological activity most, showing at least a 100-fold reduction (SA>0.2% of wt rhuHGF). Similarly, binding of this variant was also affected as it failed to compete for binding with wt rhuHGF up to 2 mg/mL. Deletion of all other Kringles (variants ΔK2, ΔK3 or ΔK4) also induces severely reduced mitogenic activity (Table I). However, the Kds of these deletion variants remained close to that observed with wt rhuHGF.

These data show that Kringles K3 and K4 are not required for receptor binding. Our data support the previous observations by Miyazawa et al., 1991 supra and Chan et al., 1991 supra, in the sense that variant N-303, which in amino acid sequence is very similar to HGF/NK2, retains the ability to compete efficiently for binding to the HGF receptor (Kd~280 pM). Furthermore, the observations that N-303 is sufficient to bind to the receptor and that the second Kringle is not required for binding the HGF receptor (in the context of the remainder of the molecule) suggest that the receptor binding domain is contained within the finger and first Kringle of huHGF. Unfortunately, we have not been able to detect expression of this variant using our polyclonal antisera suggesting that variant N-207 (deletion after the first kringle) was not expressed in 293 cells.

EXAMPLE 6

Induction of Tyrosine-Phosphorylation of the huHGF Receptor

Figure 4:
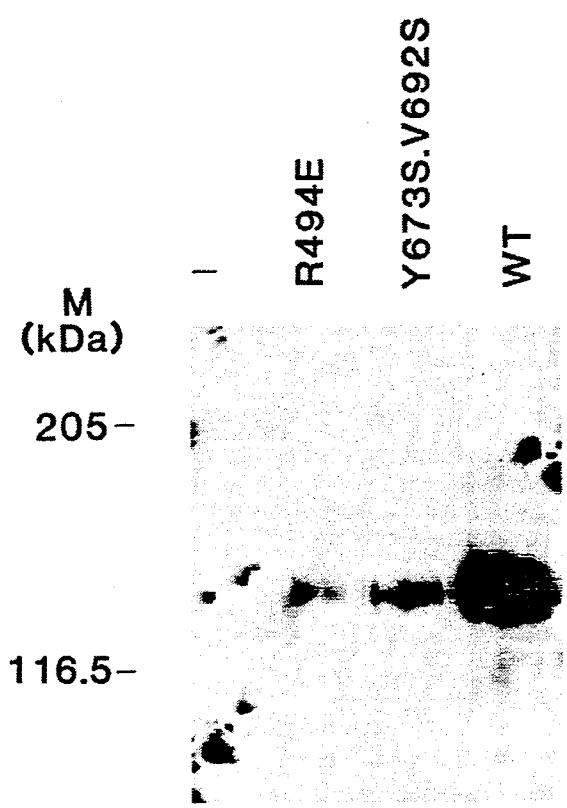
FIG. 4: Western blot of ligand-induced tyrosine-phosphorylation on the 145 kDa β-subunit of the HGF receptor by wild-type rhuHGF, single-chain or protease domain huHGF variants. Lysates from A549 cells incubated for 5 minutes without (−) or with 200 ng/mL of purified wt rhuHGF (WT), single-chain (R494E) or double protease variants (Y673S,V692S) were prepared and immunoprecipitated with an anti-HGF receptor antibody and blotted with anti-phosphotyrosine antibodies. Molecular masses (kilodaltons) are as indicated.

We determined if variants R494E or Y673S,V692S, which bind the HGF receptor in vitro but are defective for mitogenic activity, could stimulate tyrosine-phosphorylation of the HGF receptor in A549 cells. Serum starved cells were treated with purified WT rhuHGF or variants and immunoprecipitates of the HGF receptor were blotted and probed with phosphotyrosine antibodies. Stimulation with wt rhuHGF led to the phosphorylation on tyrosine of the 145 kDa β-subunit of the HGF receptor (FIG. 4). Both variants exhibited a reduced ability to induce phosphorylation of the HGF receptor.

Stimulation of tyrosine phosphorylation on the HGF receptor β-subunit by HGF was previously reported [Bottaro et al., Science 251, 802–804 (1991), Naldini et al., 1991 supra]. The present data show that variants R494E and Y673S,V692S can bind the soluble HGF receptor: IgG protein in vitro but are not efficient in stimulating tyrosine-phosphorylation in A549 cells. One interpretation of this result is that these variants are capable of binding the HGF receptor on A549 cells, but are defective in a function required to induce efficient phosphorylation, e.g. receptor dimerization. It has been shown for other receptor proteins with an intrinsic tyrosine kinase such as the epithelial and platelet-derived growth factor that receptor-receptor interactions or dimerization is required for activation of kinase function [see for review Ulrich and Schlessinger, Cell 61 203–212 (1990)]. Alternatively, these variants may not be able to bind the cell-surface associated HGF receptor.

The unique structure of HGF suggests that there may be multiple events that regulate the biological activity of this molecule. An early stage of regulation may be the cleavage step to generate the biologically active two-chain form. Interestingly, cleavage may not simply regulate receptor binding but rather control a subsequent event required for activating the HGF receptor. Our data also suggest that the β-chain, while not absolutely required for receptor binding contributes to a receptor activation step. These variants may be useful in dissecting the signalling events at the HGF receptor.

The entire contents of all citations cited throughout the specification and the references cited therein are hereby expressly incorporated by reference.

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the present invention.

TABLE 1

| Variants (var) | SA var/SA wt +/− S.D. | Kdwt/Kdvar +/− S.D. |
|---|---|---|
| Single-chain | | |
| R494A | <0.03 | 0.32 +/− 0.18 |
| R494D | <0.03 | 0.51 +/− 0.21 |
| R494E | <0.02 | 0.31 +/− 0.13 |
| Protease | | |
| Q534H | 1.19 +/− 0.44 | 1.48 +/− 0.85 |
| Y673S | 0.27 +/− 0.07* | 1.35 +/− 0.72 |
| V692S | 0.08 +/− 0.04 | 1.02 +/− 0.13 |
| Q534H, Y673S | <0.03 | 2.24 +/− 1.11 |
| Y673S, V692S | <0.02 | 1.76 +/− 0.63 |
| Q534H, Y673S, V692S | <0.02 | 1.91 +/− 1.28 |
| C-terminal truncation | | |
| N-303 | <0.05 | 0.23 +/− 0.03 |
| N-384 | <0.05 | 0.25 +/− 0.02 |
| α-chain | <0.04 | 0.25 +/− 0.03 |
| Kringle deletion | | |
| ΔK1 | <0.002 | <0.03 |
| ΔK2 | <0.05 | 0.41 +/− 0.18 |
| ΔK3 | <0.03 | 0.56 +/− 0.36 |
| ΔK4 | <0.07 | 0.86 +/− 0.46 |

We claim:

1. An isolated nucleotide molecule encoding a hepatocyte growth factor (HGF) variant having an amino acid alteration at a site within the protease domain of HGF, said variant retaining substantially full receptor binding affinity of the corresponding wild-type HGF and being substantially devoid of HGF biological activity.

2. A replicable expression vector containing and capable of expressing in a suitable host cell the nucleotide molecule of claim 1.

3. A host cell transformed with the vector of claim 2.

4. A process comprising culturing the host cells of claim 3 so as to express the nucleic acid encoding the HGF variant.

5. The process of claim 4 further comprising recovering the variant from the host cell culture.

6. An isolated nucleotide molecule encoding a human HGF (huHGF) variant having an amino acid alteration at or adjacent to position 692 of wild-type huHGF, said variant retaining substantially full receptor binding affinity of the corresponding wild-type HGF and being substantially devoid of HGF biological activity.

7. The expression vector containing and capable of expressing in a suitable host cell the nucleotide molecule of claim 6.

8. The nucleotide molecule of claim 6 encoding a huHGF variant having another amino acid substituted for valine at position 692 of the wild-type huHGF amino acid sequence.

9. The nucleotide molecule of claim 8 wherein in the encoded huHGF variant the amino acid substituted for valine at position 692 is polar.

10. The nucleotide molecule of claim 8 wherein said amino acid is selected from serine, threonine, asparagine and glutamine.

11. The nucleotide molecule of claim 10 wherein said amino acid is serine.

12. A replicable expression vector containing and capable of expressing in a suitable host cell the nucleotide molecule of claim 8.

13. A host cell transformed with the vector of claim 12.

14. A process comprising culturing the host cell of claim 13 so as to express the nucleotide molecule of claim 8.

15. The process of claim 14 further comprising recovering the variant from the host cell culture.

16. The nucleotide molecule of claim 6 wherein said huHGF variant further comprises a substitution at amino acid positions 534 or 673 of wild-type huHGF.

17. The nucleotide molecule of claim 16 encoding a huHGF variant selected from the group consisting of Y673S,V692S huHGF and Q534H,Y673S,V692S huHGF.

18. A replicable expression vector containing and capable of expressing in a suitable host cell the nucleotide molecule of claim 17.

19. A host cell transformed with the vector of claim 18.

20. A process comprising culturing the host cell of claim 19 so as to express the nucleotide molecule of claim 17.

21. The process of claim 20 further comprising recovering the variant from the host cell culture.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 4732 bases
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
TTCGAGCTCG   CCCGACATTG   ATTATTGACT   AGTTATTAAT   AGTAATCAAT    50

TACGGGGTCA   TTAGTTCATA   GCCCATATAT   GGAGTTCCGC   GTTACATAAC   100

TTACGGTAAA   TGGCCCGCCT   GGCTGACCGC   CCAACGACCC   CCGCCCATTG   150

ACGTCAATAA   TGACGTATGT   TCCCATAGTA   ACGCCAATAG   GGACTTTCCA   200

TTGACGTCAA   TGGGTGGAGT   ATTTACGGTA   AACTGCCCAC   TTGGCAGTAC   250

ATCAAGTGTA   TCATATGCCA   AGTACGCCCC   CTATTGACGT   CAATGACGGT   300

AAATGGCCCG   CCTGGCATTA   TGCCCAGTAC   ATGACCTTAT   GGGACTTTCC   350

TACTTGGCAG   TACATCTACG   TATTAGTCAT   CGCTATTACC   ATGGTGATGC   400
```

```
GGTTTTGGCA GTACATCAAT GGGCGTGGAT AGCGGTTTGA CTCACGGGGA  450
TTTCCAAGTC TCCACCCCAT TGACGTCAAT GGGAGTTTGT TTTGGCACCA  500
AAATCAACGG GACTTTCCAA AATGTCGTAA CAACTCCGCC CCATTGACGC  550
AAATGGGCGG TAGGCGTGTA CGGTGGGAGG TCTATATAAG CAGAGCTCGT  600
TTAGTGAACC GTCAGATCGC CTGGAGACGC CATCCACGCT GTTTTGACCT  650
CCATAGAAGA CACCGGGACC GATCCAGCCT CCGCGGCCGG GAACGGTGCA  700
TTGGAACGCG GATTCCCCGT GCCAAGAGTG ACGTAAGTAC CGCCTATAGA  750
GTCTATAGGC CCACCCCCTT GGCTTCGTTA GAACGCGGCT ACAATTAATA  800
CATAACCTTA TGTATCATAC ACATACGATT TAGGTGACAC TATAGAATAA  850
CATCCACTTT GCCTTTCTCT CCACAGGTGT CCACTCCCAG GTCCAACTGC  900
ACCTCGGTTC TATCGATTGA ATTCCCGGG GATCCTCTAG AGTCGACCTG  950
CAGAAGCTTG CCTCGAGGCA AGCTTGGCCG CCATGGCCCA ACTTGTTTAT  1000
TGCAGCTTAT AATGGTTACA AATAAAGCAA TAGCATCACA AATTTCACAA  1050
ATAAAGCATT TTTTTCACTG CATTCTAGTT GTGGTTTGTC CAAACTCATC  1100
AATGTATCTT ATCATGTCTG GATCGATCGG GAATTAATTC GGCGCAGCAC  1150
CATGGCCTGA AATAACCTCT GAAAGAGGAA CTTGGTTAGG TACCTTCTGA  1200
GGCGGAAAGA ACCAGCTGTG AATGTGTGT  CAGTTAGGGT GTGGAAAGTC  1250
CCCAGGCTCC CCAGCAGGCA GAAGTATGCA AAGCATGCAT CTCAATTAGT  1300
CAGCAACCAG GTGTGGAAAG TCCCCAGGCT CCCCAGCAGG CAGAAGTATG  1350
CAAAGCATGC ATCTCAATTA GTCAGCAACC ATAGTCCCGC CCCTAACTCC  1400
GCCCATCCCG CCCCTAACTC CGCCCAGTTC CGCCCATTCT CCGCCCCATG  1450
GCTGACTAAT TTTTTTTATT TATGCAGAGG CCGAGGCCGC CTCGGCCTCT  1500
GAGCTATTCC AGAAGTAGTG AGGAGGCTTT TTTGGAGGCC TAGGCTTTTG  1550
CAAAAAGCTG TTAACAGCTT GGCACTGGCC GTCGTTTTAC AACGTCGTGA  1600
CTGGGAAAAC CCTGGCGTTA CCCAACTTAA TCGCCTTGCA GCACATCCCC  1650
CCTTCGCCAG CTGGCGTAAT AGCGAAGAGG CCCGCACCGA TCGCCCTTCC  1700
CAACAGTTGC GTAGCCTGAA TGGCGAATGG CGCCTGATGC GGTATTTTCT  1750
CCTTACGCAT CTGTGCGGTA TTTCACACCG CATACGTCAA AGCAACCATA  1800
GTACGCGCCC TGTAGCGGCG CATTAAGCGC GGCGGGTGTG GTGGTTACGC  1850
GCAGCGTGAC CGCTACACTT GCCAGCGCCC TAGCGCCCGC TCCTTTCGCT  1900
TTCTTCCCTT CCTTTCTCGC CACGTTCGCC GGCTTTCCCC GTCAAGCTCT  1950
AAATCGGGGG CTCCCTTTAG GGTTCCGATT TAGTGCTTTA CGGCACCTCG  2000
ACCCCAAAAA ACTTGATTTG GGTGATGGTT CACGTAGTGG GCCATCGCCC  2050
TGATAGACGG TTTTTCGCCC TTTGACGTTG GAGTCCACGT TCTTTAATAG  2100
TGGACTCTTG TTCCAAACTG GAACAACACT CAACCCTATC TCGGGCTATT  2150
CTTTTGATTT ATAAGGGATT TTGCCGATTT CGGCCTATTG GTTAAAAAAT  2200
GAGCTGATTT AACAAAAATT TAACGCGAAT TTTAACAAAA TATTAACGTT  2250
TACAATTTTA TGGTGCACTC TCAGTACAAT CTGCTCTGAT GCCGCATAGT  2300
TAAGCCAACT CCGCTATCGC TACGTGACTG GGTCATGGCT GCGCCCCGAC  2350
ACCCGCCAAC ACCCGCTGAC GCGCCCTGAC GGGCTTGTCT GCTCCCGGCA  2400
TCCGCTTACA GACAAGCTGT GACCGTCTCC GGGAGCTGCA TGTGTCAGAG  2450
```

```
GTTTTCACCG TCATCACCGA AACGCGCGAG GCAGTATTCT TGAAGACGAA    2500

AGGGCCTCGT GATACGCCTA TTTTTATAGG TTAATGTCAT GATAATAATG    2550

GTTTCTTAGA CGTCAGGTGG CACTTTTCGG GGAAATGTGC GCGGAACCCC    2600

TATTTGTTTA TTTTTCTAAA TACATTCAAA TATGTATCCG CTCATGAGAC    2650

AATAACCCTG ATAAATGCTT CAATAATATT GAAAAGGAA GAGTATGAGT    2700

ATTCAACATT TCCGTGTCGC CCTTATTCCC TTTTTGCGG CATTTGCCT    2750

TCCTGTTTTT GCTCACCCAG AAACGCTGGT GAAAGTAAAA GATGCTGAAG    2800

ATCAGTTGGG TGCACGAGTG GGTTACATCG AACTGGATCT CAACAGCGGT    2850

AAGATCCTTG AGAGTTTTCG CCCCGAAGAA CGTTTTCCAA TGATGAGCAC    2900

TTTTAAAGTT CTGCTATGTG GCGCGGTATT ATCCCGTGAT GACGCCGGGC    2950

AAGAGCAACT CGGTCGCCGC ATACACTATT CTCAGAATGA CTTGGTTGAG    3000

TACTCACCAG TCACAGAAAA GCATCTTACG GATGGCATGA CAGTAAGAGA    3050

ATTATGCAGT GCTGCCATAA CCATGAGTGA TAACACTGCG GCCAACTTAC    3100

TTCTGACAAC GATCGGAGGA CCGAAGGAGC TAACCGCTTT TTTGCACAAC    3150

ATGGGGGATC ATGTAACTCG CCTTGATCGT TGGGAACCGG AGCTGAATGA    3200

AGCCATACCA AACGACGAGC GTGACACCAC GATGCCAGCA GCAATGGCAA    3250

CAACGTTGCG CAAACTATTA ACTGGCGAAC TACTTACTCT AGCTTCCCGG    3300

CAACAATTAA TAGACTGGAT GGAGGCGGAT AAAGTTGCAG GACCACTTCT    3350

GCGCTCGGCC CTTCCGGCTG GCTGGTTTAT TGCTGATAAA TCTGGAGCCG    3400

GTGAGCGTGG GTCTCGCGGT ATCATTGCAG CACTGGGGCC AGATGGTAAG    3450

CCCTCCCGTA TCGTAGTTAT CTACACGACG GGGAGTCAGG CAACTATGGA    3500

TGAACGAAAT AGACAGATCG CTGAGATAGG TGCCTCACTG ATTAAGCATT    3550

GGTAACTGTC AGACCAAGTT TACTCATATA TACTTTAGAT TGATTTAAAA    3600

CTTCATTTTT AATTTAAAAG GATCTAGGTG AAGATCCTTT TTGATAATCT    3650

CATGACCAAA ATCCCTTAAC GTGAGTTTTC GTTCCACTGA GCGTCAGACC    3700

CCGTAGAAAA GATCAAAGGA TCTTCTTGAG ATCCTTTTTT TCTGCGCGTA    3750

ATCTGCTGCT TGCAAACAAA AAACCACCG CTACCAGCGG TGGTTTGTTT    3800

GCCGGATCAA GAGCTACCAA CTCTTTTTCC GAAGGTAACT GGCTTCAGCA    3850

GAGCGCAGAT ACCAAATACT GTCCTTCTAG TGTAGCCGTA GTTAGGCCAC    3900

CACTTCAAGA ACTCTGTAGC ACCGCCTACA TACCTCGCTC TGCTAATCCT    3950

GTTACCAGTG GCTGCTGCCA GTGGCGATAA GTCGTGTCTT ACCGGGTTGG    4000

ACTCAAGACG ATAGTTACCG GATAAGGCGC AGCGGTCGGG CTGAACGGGG    4050

GGTTCGTGCA CACAGCCCAG CTTGGAGCGA ACGACCTACA CCGAACTGAG    4100

ATACCTACAG CGTGAGCATT GAGAAAGCGC CACGCTTCCC GAAGGGAGAA    4150

AGGCGGACAG GTATCCGGTA AGCGGCAGGG TCGGAACAGG AGAGCGCACG    4200

AGGGAGCTTC CAGGGGGAAA CGCCTGGTAT CTTTATAGTC CTGTCGGGTT    4250

TCGCCACCTC TGACTTGAGC GTCGATTTTT GTGATGCTCG TCAGGGGGGC    4300

GGAGCCTATG GAAAAACGCC AGCAACGCGG CCTTTTTACG GTTCCTGGCC    4350

TTTTGCTGGC CTTTTGCTCA CATGTTCTTT CCTGCGTTAT CCCCTGATTC    4400

TGTGGATAAC CGTATTACCG CCTTTGAGTG AGCTGATACC GCTCGCCGCA    4450

GCCGAACGAC CGAGCGCAGC GAGTCAGTGA GCGAGGAAGC GGAAGAGCGC    4500
```

```
CCAATACGCA AACCGCCTCT CCCCGCGCGT TGGCCGATTC ATTAATCCAG    4550

CTGGCACGAC AGGTTTCCCG ACTGGAAAGC GGGCAGTGAG CGCAACGCAA    4600

TTAATGTGAG TTACCTCACT CATTAGGCAC CCCAGGCTTT ACACTTTATG    4650

CTTCCGGCTC GTATGTTGTG TGGAATTGTG AGCGGATAAC AATTTCACAC    4700

AGGAAACAGC TATGACCATG ATTACGAATT AA    4732
```

( 2 ) INFORMATION FOR SEQ ID NO:2:

( i ) SEQUENCE CHARACTERISTICS:
        ( A ) LENGTH: 47 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
TTGGAATCCC ATTTACAACC TCGAGTTGTT TCGTTTTGGC ACAAGAT    47
```

( 2 ) INFORMATION FOR SEQ ID NO:3:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
GAATCCCATT TACGACGTCC AATTGTTTCG    30
```

( 2 ) INFORMATION FOR SEQ ID NO:4:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
CCCATTTACA ACTGCCAATT GTTTCG    26
```

( 2 ) INFORMATION FOR SEQ ID NO:5:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
AGAAGGGAAA CAGTGTCGTG CA    22
```

( 2 ) INFORMATION FOR SEQ ID NO:6:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
AGTGGGCCAC CAGAATCCCC CT    22
```

( 2 ) INFORMATION FOR SEQ ID NO:7:

( i ) SEQUENCE CHARACTERISTICS:
        ( A ) LENGTH: 23 bases
        ( B ) TYPE: nucleic acid (C) STRANDEDNESS: single
(D) TOPOLOGY: linear (xi) SEQUENCE DESCRIPTION: SEQ ID NO:7:

TCCACGACCA GGAGAAATGA CAC    23

(2) INFORMATION FOR SEQ ID NO:8:

(i) SEQUENCE CHARACTERISTICS:
(A) LENGTH: 30 bases
(B) TYPE: nucleic acid
(C) STRANDEDNESS: single
(D) TOPOLOGY: linear (xi) SEQUENCE DESCRIPTION: SEQ ID NO:8:

GCATTCAACT TCTGAGTTTC TAATGTAGTC    30

(2) INFORMATION FOR SEQ ID NO:9:

(i) SEQUENCE CHARACTERISTICS:
(A) LENGTH: 30 bases
(B) TYPE: nucleic acid
(C) STRANDEDNESS: single
(D) TOPOLOGY: linear (xi) SEQUENCE DESCRIPTION: SEQ ID NO:9:

CATAGTATTG TCAGCTTCAA CTTCTGAACA    30

(2) INFORMATION FOR SEQ ID NO:10:

(i) SEQUENCE CHARACTERISTICS:
(A) LENGTH: 30 bases
(B) TYPE: nucleic acid
(C) STRANDEDNESS: single
(D) TOPOLOGY: linear (xi) SEQUENCE DESCRIPTION: SEQ ID NO:10:

TCCATGTGAC ATATCTTCAG TTGTTTCCAA    30

(2) INFORMATION FOR SEQ ID NO:11:

(i) SEQUENCE CHARACTERISTICS:
(A) LENGTH: 30 bases
(B) TYPE: nucleic acid
(C) STRANDEDNESS: single
(D) TOPOLOGY: linear (xi) SEQUENCE DESCRIPTION: SEQ ID NO:11:

TGTGGTATCA CCTTCATCTT GTCCATGTGA    30

(2) INFORMATION FOR SEQ ID NO:12:

(i) SEQUENCE CHARACTERISTICS:
(A) LENGTH: 24 bases
(B) TYPE: nucleic acid
(C) STRANDEDNESS: single
(D) TOPOLOGY: linear (xi) SEQUENCE DESCRIPTION: SEQ ID NO:12:

ACCTTGGATG CATTAAGTTG TTTC    24

(2) INFORMATION FOR SEQ ID NO:13:

(i) SEQUENCE CHARACTERISTICS:
(A) LENGTH: 23 bases
(B) TYPE: nucleic acid
(C) STRANDEDNESS: single
(D) TOPOLOGY: linear (xi) SEQUENCE DESCRIPTION: SEQ ID NO:13:

TTGTCCATGT GATTAATCAC AGT 23

( 2 ) INFORMATION FOR SEQ ID NO:14:

( i ) SEQUENCE CHARACTERISTICS:
        ( A ) LENGTH: 35 bases
        ( B ) TYPE: nucleic acid
        ( C ) STRANDEDNESS: single
        ( D ) TOPOLOGY: linear ( x i ) SEQUENCE DESCRIPTION: SEQ ID NO:14:

GTTCGTGTTG GGATCCCATT TACCTATCGC AATTG 35

( 2 ) INFORMATION FOR SEQ ID NO:15:

( i ) SEQUENCE CHARACTERISTICS:
        ( A ) LENGTH: 10596 bases
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
TTCGAGCTCG CCCGACATTG ATTATTGACT AGTTATTAAT AGTAATCAAT  50
TACGGGGTCA TTAGTTCATA GCCCATATAT GGAGTTCCGC GTTACATAAC  100
TTACGGTAAA TGGCCCGCCT GGCTGACCGC CCAACGACCC CCGCCCATTG  150
ACGTCAATAA TGACGTATGT TCCCATAGTA ACGCCAATAG GGACTTTCCA  200
TTGACGTCAA TGGGTGGAGT ATTTACGGTA AACTGCCCAC TTGGCAGTAC  250
ATCAAGTGTA TCATATGCCA AGTACGCCCC CTATTGACGT CAATGACGGT  300
AAATGGCCCG CCTGGCATTA TGCCCAGTAC ATGACCTTAT GGGACTTTCC  350
TACTTGGCAG TACATCTACG TATTAGTCAT CGCTATTACC ATGGTGATGC  400
GGTTTTGGCA GTACATCAAT GGGCGTGGAT AGCGGTTTGA CTCACGGGGA  450
TTTCCAAGTC TCCACCCCAT TGACGTCAAT GGGAGTTTGT TTTGGCACCA  500
AAATCAACGG GACTTTCCAA AATGTCGTAA CAACTCCGCC CCATTGACGC  550
AAATGGGCGG TAGGCGTGTA CGGTGGGAGG TCTATATAAG CAGAGCTCGT  600
TTAGTGAACC GTCAGATCGC CTGGAGACGC CATCCACGCT GTTTTGACCT  650
CCATAGAAGA CACCGGGACC GATCCAGCCT CCGCGGCCGG GAACGGTGCA  700
TTGGAACGCG GATTCCCCGT GCCAAGAGTG ACGTAAGTAC CGCCTATAGA  750
GTCTATAGGC CCACCCCCTT GGCTTCGTTA GAACGCGGCT ACAATTAATA  800
CATAACCTTA TGTATCATAC ACATACGATT TAGGTGACAC TATAGAATAA  850
CATCCACTTT GCCTTTCTCT CCACAGGTGT CCACTCCCAG GTCCAACTGC  900
ACCTCGGTTC TATCGATTCT CGAGAATTAA TTCAAGCTTG CGGCCGCAGC  950
TTGGCCGCCA TGGCCCAACT TGTTTATTGC AGCTTATAAT GGTTACAAAT  1000
AAAGCAATAG CATCACAAAT TTCACAAATA AAGCATTTTT TCACTGCAT   1050
TCTAGTTGTG GTTTGTCCAA ACTCATCAAT GTATCTTATC ATGTCTGGAT  1100
CGATCGGGAA TTAATTCGGC GCAGCACCAT GGCCTGAAAT AACCTCTGAA  1150
AGAGGAACTT GGTTAGGTAC CTTCTGAGGC GGAAAGAACC AGCTGTGGAA  1200
TGTGTGTCAG TTAGGGTGTG AAAGTCCCC  AGGCTCCCCA GCAGGCAGAA  1250
GTATGCAAAG CATGCATCTC AATTAGTCAG CAACCAGGTG TGGAAAGTCC  1300
CCAGGCTCCC CAGCAGGCAG AAGTATGCAA AGCATGCATC TCAATTAGTC  1350
AGCAACCATA GTCCCGCCCC TAACTCCGCC CATCCCGCCC CTAACTCCGC  1400
```

```
CCAGTTCCGC  CCATTCTCCG  CCCCATGGCT  GACTAATTTT  TTTTATTTAT  1450
GCAGAGGCCG  AGGCCGCCTC  GGCCTCTGAG  CTATTCCAGA  AGTAGTGAGG  1500
AGGCTTTTTT  GGAGGCCTAG  GCTTTTGCAA  AAAGCTGTTC  ACGTGATGAA  1550
TTCTCATGTT  TGACAGCTTA  TCATCGATAG  ATCCTCACAG  GCCGCACCCA  1600
GCTTTTCTTC  CGTTGCCCCA  GTAGCATCTC  TGTCTGGTGA  CCTTGAAGAG  1650
GAAGAGGAGG  GGTCCCGAGA  ATCCCCATCC  CTACCGTCCA  GCAAAAGGG   1700
GGACGAGGAA  TTTGAGGCCT  GGCTTGAGGC  TCAGGACGCA  AATCTTGAGG  1750
ATGTTCAGCG  GGAGTTTTCC  GGGCTGCGAG  TAATTGGTGA  TGAGGACGAG  1800
GATGGTTCGG  AGGATGGGGA  ATTTTCAGAC  CTGGATCTGT  CTGACAGCGA  1850
CCATGAAGGG  GATGAGGGTG  GGGGGGCTGT  TGGAGGGGGC  AGGAGTCTGC  1900
ACTCCCTGTA  TTCACTGAGC  GTCGTCTAAT  AAAGATGTCT  ATTGATCTCT  1950
TTTAGTGTGA  ATCATGTCTG  ACGAGGGGCC  AGGTACAGGA  CCTGGAAATG  2000
GCCTAGGAGA  GAAGGGAGAC  ACATCTGGAC  CAGAAGGCTC  CGGCGGCAGT  2050
GGACCTCAAA  GAAGAGGGGG  TGATAACCAT  GGACGAGGAC  GGGGAAGAGG  2100
ACGAGGACGA  GGAGGCGGAA  GACCAGGAGC  CCCGGGCGGC  TCAGGATCAG  2150
GGCCAAGACA  TAGAGATGGT  GTCCGGAGAC  CCCAAAAACG  TCCAAGTTGC  2200
ATTGGCTGCA  AAGGGACCCA  CGGTGGAACA  GGAGCAGGAG  CAGGAGCGGG  2250
AGGGGCAGGA  GCAGGAGGGG  CAGGAGCAGG  AGGAGGGGCA  GGAGCAGGAG  2300
GAGGGGCAGG  AGGGGCAGGA  GGGGCAGGAG  GGCAGGAGC   AGGAGGAGGG  2350
GCAGGAGCAG  GAGGAGGGGC  AGGAGGGGCA  GGAGGGGCAG  GAGCAGGAGG  2400
AGGGGCAGGA  GCAGGAGGAG  GGCAGGAGG   GGCAGGAGCA  GGAGGAGGGG  2450
CAGGAGGGGC  AGGAGGGGCA  GGAGCAGGAG  GAGGGGCAGG  AGCAGGAGGA  2500
GGGGCAGGAG  GGGCAGGAGC  AGGAGGAGGG  GCAGGAGGGG  CAGGAGGGGC  2550
AGGAGCAGGA  GGAGGGGCAG  GAGCAGGAGG  GGCAGGAGGG  GCAGGAGGGG  2600
CAGGAGCAGG  AGGGGCAGGA  GCAGGAGGAG  GGGCAGGAGG  GGCAGGAGGG  2650
GCAGGAGCAG  GAGGGGCAGG  AGCAGGAGGG  GCAGGAGCAG  GAGGGGCAGG  2700
AGCAGGAGGG  GCAGGAGGGG  CAGGAGCAGG  AGGGGCAGGA  GGGGCAGGAG  2750
CAGGAGGGGC  AGGAGGGGCA  GGAGCAGGAG  GAGGGGCAGG  AGGGGCAGGA  2800
GCAGGAGGAG  GGGCAGGAGG  GGCAGGAGCA  GGAGGGGCAG  GAGGGGCAGG  2850
AGCAGGAGGG  GCAGGAGGGG  CAGGAGCAGG  AGGGGCAGGA  GGGGCAGGAG  2900
CAGGAGGAGG  GGCAGGAGCA  GGAGGGGCAG  GAGCAGGAGG  TGGAGGCCGG  2950
GGTCGAGGAG  GCAGTGGAGG  CCGGGGTCGA  GGAGGTAGTG  GAGGCCGGGG  3000
TCGAGGAGGT  AGTGGAGGCC  GCCGGGGTAG  AGGACGTGAA  AGAGCCAGGG  3050
GGGGAAGTCG  TGAAAGAGCC  AGGGGGAGAG  GTCGTGGACG  TGGAGAAAAG  3100
AGGCCCAGGA  GTCCCAGTAG  TCAGTCATCA  TCATCCGGGT  CTCCACCGCG  3150
CAGGCCCCCT  CCAGGTAGAA  GGCCATTTTT  CCACCCTGTA  GGGGAAGCCG  3200
ATTATTTTGA  ATACCACCAA  GAAGGTGGCC  CAGATGGTGA  GCCTGACGTG  3250
CCCCCGGGAG  CGATAGAGCA  GGGCCCCGCA  GATGACCCAG  GAGAAGGCCC  3300
AAGCACTGGA  CCCCGGGGTC  AGGGTGATGG  AGGCAGGCGC  AAAAAAGGAG  3350
GGTGGTTTGG  AAAGCATCGT  GGTCAAGGAG  GTTCCAACCC  GAAATTTGAG  3400
AACATTGCAG  AAGGTTTAAG  AGCTCTCCTG  GCTAGGAGTC  ACGTAGAAAG  3450
```

```
GACTACCGAC  GAAGGAACTT  GGGTCGCCGG  TGTGTTCGTA  TATGGAGGTA  3500
GTAAGACCTC  CCTTTACAAC  CTAAGGCGAG  GAACTGCCCT  TGCTATTCCA  3550
CAATGTCGTC  TTACACCATT  GAGTCGTCTC  CCCTTTGGAA  TGGCCCCTGG  3600
ACCCGGCCCA  CAACCTGGCC  CGCTAAGGGA  GTCCATTGTC  TGTTATTTCA  3650
TGGTCTTTTT  ACAAACTCAT  ATATTTGCTG  AGGTTTTGAA  GGATGCGATT  3700
AAGGACCTTG  TTATGACAAA  GCCCGCTCCT  ACCTGCAATA  TCAGGGTGAC  3750
TGTGTGCAGC  TTTGACGATG  GAGTAGATTT  GCCTCCCTGG  TTTCCACCTA  3800
TGGTGGAAGG  GGCTGCCGCG  GAGGGTGATG  ACGGAGATGA  CGGAGATGAA  3850
GGAGGTGATG  GAGATGAGGG  TGAGGAAGGG  CAGGAGTGAT  GTAACTTGTT  3900
AGGAGACGCC  CTCAATCGTA  TTAAAAGCCG  TGTATTCCCC  CGCACTAAAG  3950
AATAAATCCC  CAGTAGACAT  CATGCGTGCT  GTTGGTGTAT  TTCTGGCCAT  4000
CTGTCTTGTC  ACCATTTTCG  TCCTCCCAAC  ATGGGGCAAT  TGGGCATACC  4050
CATGTTGTCA  CGTCACTCAG  CTCCGCGCTC  AACACCTTCT  CGCGTTGGAA  4100
AACATTAGCG  ACATTTACCT  GGTGAGCAAT  CAGACATGCG  ACGGCTTTAG  4150
CCTGGCCTCC  TTAAATTCAC  CTAAGAATGG  GAGCAACCAG  CATGCAGGAA  4200
AAGGACAAGC  AGCGAAAATT  CACGCCCCCT  TGGGAGGTGG  CGGCATATGC  4250
AAAGGATAGC  ACTCCCACTC  TACTACTGGG  TATCATATGC  TGACTGTATA  4300
TGCATGAGGA  TAGCATATGC  TACCCGGATA  CAGATTAGGA  TAGCATATAC  4350
TACCCAGATA  TAGATTAGGA  TAGCATATGC  TACCCAGATA  TAGATTAGGA  4400
TAGCCTATGC  TACCCAGATA  TAAATTAGGA  TAGCATATAC  TACCCAGATA  4450
TAGATTAGGA  TAGCATATGC  TACCCAGATA  TAGATTAGGA  TAGCCTATGC  4500
TACCCAGATA  TAGATTAGGA  TAGCATATGC  TACCCAGATA  TAGATTAGGA  4550
TAGCATATGC  TATCCAGATA  TTTGGGTAGT  ATATGCTACC  CAGATATAAA  4600
TTAGGATAGC  ATATACTACC  CTAATCTCTA  TTAGGATAGC  ATATGCTACC  4650
CGGATACAGA  TTAGGATAGC  ATATACTACC  CAGATATAGA  TTAGGATAGC  4700
ATATGCTACC  CAGATATAGA  TTAGGATAGC  CTATGCTACC  CAGATATAAA  4750
TTAGGATAGC  ATATACTACC  CAGATATAGA  TTAGGATAGC  ATATGCTACC  4800
CAGATATAGA  TTAGGATAGC  CTATGCTACC  CAGATATAGA  TTAGGATAGC  4850
ATATGCTATC  CAGATATTTG  GGTAGTATAT  GCTACCCATG  GCAACATTAG  4900
CCCACCGTGC  TCTCAGCGAC  CTCGTGAATA  TGAGGACCAA  CAACCCTGTG  4950
CTTGGCGCTC  AGGCGCAAGT  GTGTGTAATT  TGTCCTCCAG  ATCGCAGCAA  5000
TCGCGCCCCT  ATCTTGGCCC  GCCCACCTAC  TTATGCAGGT  ATTCCCCGGG  5050
GTGCCATTAG  TGGTTTTGTG  GGCAAGTGGT  TTGACCGCAG  TGGTTAGCGG  5100
GGTTACAATC  AGCCAAGTTA  TTACACCCTT  ATTTTACAGT  CCAAAACCGC  5150
AGGGCGGCGT  GTGGGGGCTG  ACGCGTGCCC  CCACTCCACA  ATTTCAAAAA  5200
AAAGAGTGGC  CACTTGTCTT  TGTTTATGGG  CCCCATTGGC  GTGGAGCCCC  5250
GTTTAATTTT  CGGGGGTGTT  AGAGACAACC  AGTGGAGTCC  GCTGCTGTCG  5300
GCGTCCACTC  TCTTTCCCCT  TGTTACAAAT  AGAGTGTAAC  AACATGGTTC  5350
ACCTGTCTTG  GTCCCTGCCT  GGGACACATC  TTAATAACCC  CAGTATCATA  5400
TTGCACTAGG  ATTATGTGTT  GCCCATAGCC  ATAAATTCGT  GTGAGATGGA  5450
CATCCAGTCT  TTACGGCTTG  TCCCCACCCC  ATGGATTTCT  ATTGTTAAAG  5500
```

```
ATATTCAGAA TGTTTCATTC CTACACTAGT ATTTATTGCC CAAGGGGTTT   5550
GTGAGGGTTA TATTGGTGTC ATAGCACAAT GCCACCACTG AACCCCCCGT   5600
CCAAATTTTA TTCTGGGGGC GTCACCTGAA ACCTTGTTTT CGAGCACCTC   5650
ACATACACCT TACTGTTCAC AACTCAGCAG TTATTCTATT AGCTAAACGA   5700
AGGAGAATGA AGAAGCAGGC GAAGATTCAG GAGAGTTCAC TGCCCGCTCC   5750
TTGATCTTCA GCCACTGCCC TTGTGACTAA AATGGTTCAC TACCCTCGTG   5800
GAATCCTGAC CCCATGTAAA TAAAACCGTG ACAGCTCATG GGTGGGAGA    5850
TATCGCTGTT CCTTAGGACC CTTTTACTAA CCCTAATTCG ATAGCATATG   5900
CTTCCCGTTG GGTAACATAT GCTATTGAAT TAGGGTTAGT CTGGATAGTA   5950
TATACTACTA CCCGGGAAGC ATATGCTACC CGTTTAGGGT TAACAAGGGG   6000
GCCTTATAAA CACTATTGCT AATGCCCTCT TGAGGGTCCG CTTATCGGTA   6050
GCTACACAGG CCCCTCTGAT TGACGTTGGT GTAGCCTCCC GTAGTCTTCC   6100
TGGGCCCCTG GGAGGTACAT GTCCCCAGC ATTGGTGTAA GAGCTTCAGC    6150
CAAGAGTTAC ACATAAAGGC AATGTTGTGT TGCAGTCCAC AGACTGCAAA   6200
GTCTGCTCCA GGATGAAAGC CACTCAGTGT TGGCAAATGT GCACATCCAT   6250
TTATAAGGAT GTCAACTACA GTCAGAGAAC CCCTTTGTGT TTGGTCCCCC   6300
CCCGTGTCAC ATGTGGAACA GGGCCCAGTT GGCAAGTTGT ACCAACCAAC   6350
TGAAGGGATT ACATGCACTG CCCGTGACCA ATACAAAACA AAAGCGCTCC   6400
TCGTACCAGC GAAGAAGGGG CAGAGATGCC GTAGTCAGGT TTAGTTCGTC   6450
CGGCGGCGGG GGATCCGCCA GAAATCCGCG CGGTGGTTTT TGGGGTCGG    6500
GGGTGTTTGG CAGCCACAGA CGCCCGGTGT TCGTGTCGCG CCAGTACATG   6550
CGGTCCATGC CCAGGCCATC CAAAAACCAT GGGTCTGTCT GCTCAGTCCA   6600
GTCGTGGACC TGACCCCACG CAACGCCCAA AAGAATAACC CCACGAACC    6650
ATAAACCATT CCCCATGGGG GACCCCGTCC CTAACCCACG GGGCCCGTGG   6700
CTATGGCGGG CTTGCCGCCC CGACGTTGGC TGCGAGCCCT GGGCCTTCAC   6750
CCGAACTTGG GGGTTGGGGT GGGGAAAAGG AAGAAACGCG GGCGTATTGG   6800
CCCCAATGGG GTCTCGGTGG GGTATCGACA GAGTGCCAGC CCTGGGACCG   6850
AACCCCGCGT TTATGAACAA ACGACCCAAC ACCCGTGCGT TTTATTCTGT   6900
CTTTTTATTG CCGTCATAGC GCGGGTTCCT TCCGGTATTG TCTCCTTCCG   6950
TGTTTCAGTT AGCCTCCCCC ATCTCCCGGG GTGGGCGAAG AACTCCAGCA   7000
TGAGATCCCC GCGCTGGAGG ATCATCCAGC CGGCGTCCCG GAAAACGATT   7050
CCGAAGCCCA ACCTTTCATA GAAGGCGGCG GTGGAATCGA AATCTCGTGA   7100
TGGCAGGTTG GGCGTCGCTT GGTCGGTCAT TTCGAACCCC AGAGTCCCGC   7150
TCAGAAGAAC TCGTCAAGAA GGCGATAGAA GGCGATGCGC TGCGAATCGG   7200
GAGCGGCGAT ACCGTAAAGC ACGAGGAAGC GGTCAGCCCA TTCGCCGCCA   7250
AGCTCTTCAG CAATATCACG GGTAGCCAAC GCTATGTCCT GATAGCGGTC   7300
CGCCACACCC AGCCGGCCAC AGTCGATGAA TCCAGAAAAG CGGCCATTTT   7350
CCACCATGAT ATTCGGCAAG CAGGCATCGC CATGGGTCAC GACGAGATCC   7400
TCGCCGTCGG GCATGCGCGC CTTGAGCCTG GCGAACAGTT CGGCTGGCGC   7450
GAGCCCCTGA TGCTCTTCGT CCAGATCATC CTGATCGACA AGACCGGCTT   7500
CCATCCGAGT ACGTGCTCGC TCGATGCGAT GTTTCGCTTG GTGGTCGAAT   7550
```

```
GGGCAGGTAG CCGGATCAAG CGTATGCAGC CGCCGCATTG CATCAGCCAT 7600
GATGGATACT TTCTCGGCAG GAGCAAGGTG AGATGACAGG AGATCCTGCC 7650
CCGGCACTTC GCCCAATAGC AGCCAGTCCC TTCCCGCTTC AGTGACAACG 7700
TCGAGCACAG CTGCGCAAGG AACGCCCGTC GTGGCCAGCC ACGATAGCCG 7750
CGCTGCCTCG TCCTGCAGTT CATTCAGGGC ACCGGACAGG TCGGTCTTGA 7800
CAAAAAGAAC CGGGCGCCCC TGCGCTGACA GCCGGAACAC GGCGGCATCA 7850
GAGCAGCCGA TTGTCTGTTG TGCCCAGTCA TAGCCGAATA GCCTCTCCAC 7900
CCAAGCGGCC GGAGAACCTG CGTGCAATCC ATCTTGTTCA ATCATGCGAA 7950
ACGATCCTCA TCCTGTCTCT TGATCAGATC TGCGGCACGC TGTTGACGCT 8000
GTTAAGCGGG TCGCTGCAGG GTCGCTCGGT GTTCGAGGCC ACACGCGTCA 8050
CCTTAATATG CGAAGTGGAC CTGGGACCGC GCCGCCCCGA CTGCATCTGC 8100
GTGTTCGAAT TCATCAAAGC AACCATAGTA CGCGCCCTGT AGCGGCGCAT 8150
TAAGCGCGGC GGGTGTGGTG GTTACGCGCA GCGTGACCGC TACACTTGCC 8200
AGCGCCCTAG CGCCCGCTCC TTTCGCTTTC TTCCCTTCCT TTCTCGCCAC 8250
GTTCGCCGGC TTTCCCCGTC AAGCTCTAAA TCGGGGGCTC CCTTTAGGGT 8300
TCCGATTTAG TGCTTTACGG CACCTCGACC CCAAAAAACT TGATTTGGGT 8350
GATGGTTCAC GTAGTGGGCC ATCGCCCTGA TAGACGGTTT TTCGCCCTTT 8400
GACGTTGGAG TCCACGTTCT TTAATAGTGG ACTCTTGTTC CAAACTGGAA 8450
CAACACTCAA CCCTATCTCG GCTATTCTT TTGATTTATA AGGGATTTTG 8500
CCGATTTCGG CCTATTGGTT AAAAAATGAG CTGATTTAAC AAAAATTTAA 8550
CGCGAATTTT AACAAATAT TAACGTTTAC AATTTTATGG TGCAGGCCTC 8600
GTGATACGCC TATTTTTATA GGTTAATGTC ATGATAATAA TGGTTTCTTA 8650
GACGTCAGGT GGCACTTTTC GGGGAAATGT GCGCGGAACC CCTATTTGTT 8700
TATTTTTCTA AATACATTCA AATATGTATC CGCTCATGAG ACAATAACCC 8750
TGATAAATGC TTCAATAATA TTGAAAAAGG AAGAGTATGA GTATTCAACA 8800
TTTCCGTGTC GCCCTTATTC CCTTTTTTGC GGCATTTTGC CTTCCTGTTT 8850
TTGCTCACCC AGAAACGCTG GTGAAAGTAA AAGATGCTGA AGATCAGTTG 8900
GGTGCACGAG TGGGTTACAT CGAACTGGAT CTCAACAGCG GTAAGATCCT 8950
TGAGAGTTTT CGCCCCGAAG AACGTTTTCC AATGATGAGC ACTTTTAAAG 9000
TTCTGCTATG TGGCGCGGTA TTATCCCGTG ATGACGCCGG GCAAGAGCAA 9050
CTCGGTCGCC GCATACACTA TTCTCAGAAT GACTTGGTTG AGTACTCACC 9100
AGTCACAGAA AAGCATCTTA CGGATGGCAT GACAGTAAGA GAATTATGCA 9150
GTGCTGCCAT AACCATGAGT GATAACACTG CGGCCAACTT ACTTCTGACA 9200
ACGATCGGAG GACCGAAGGA GCTAACCGCT TTTTTGCACA ACATGGGGGA 9250
TCATGTAACT CGCCTTGATC GTTGGGAACC GGAGCTGAAT GAAGCCATAC 9300
CAAACGACGA GCGTGACACC ACGATGCCAG CAGCAATGGC AACAACGTTG 9350
CGCAAACTAT TAACTGGCGA ACTACTTACT CTAGCTTCCC GGCAACAATT 9400
AATAGACTGG ATGGAGGCGG ATAAAGTTGC AGGACCACTT CTGCGCTCGG 9450
CCCTTCCGGC TGGCTGGTTT ATTGCTGATA AATCTGGAGC CGGTGAGCGT 9500
GGGTCTCGCG GTATCATTGC AGCACTGGGG CCAGATGGTA AGCCCTCCCG 9550
TATCGTAGTT ATCTACACGA CGGGGAGTCA GGCAACTATG GATGAACGAA 9600
```

```
ATAGACAGAT CGCTGAGATA GGTGCCTCAC TGATTAAGCA TTGGTAACTG    9650

TCAGACCAAG TTTACTCATA TATACTTTAG ATTGATTTAA AACTTCATTT    9700

TTAATTTAAA AGGATCTAGG TGAAGATCCT TTTTGATAAT CTCATGACCA    9750

AAATCCCTTA ACGTGAGTTT TCGTTCCACT GAGCGTCAGA CCCCGTAGAA    9800

AAGATCAAAG GATCTTCTTG AGATCCTTTT TTTCTGCGCG TAATCTGCTG    9850

CTTGCAAACA AAAAACCAC  CGCTACCAGC GGTGGTTTGT TTGCCGGATC    9900

AAGAGCTACC AACTCTTTTT CCGAAGGTAA CTGGCTTCAG CAGAGCGCAG    9950

ATACCAAATA CTGTCCTTCT AGTGTAGCCG TAGTTAGGCC ACCACTTCAA   10000

GAACTCTGTA GCACCGCCTA CATACCTCGC TCTGCTAATC CTGTTACCAG   10050

TGGCTGCTGC CAGTGGCGAT AAGTCGTGTC TTACCGGGTT GGACTCAAGA   10100

CGATAGTTAC CGGATAAGGC GCAGCGGTCG GGCTGAACGG GGGGTTCGTG   10150

CACACAGCCC AGCTTGGAGC GAACGACCTA CACCGAACTG AGATACCTAC   10200

AGCGTGAGCA TTGAGAAAGC GCCACGCTTC CCGAAGGGAG AAAGGCGGAC   10250

AGGTATCCGG TAAGCGGCAG GGTCGGAACA GGAGAGCGCA CGAGGGAGCT   10300

TCCAGGGGGA AACGCCTGGT ATCTTTATAG TCCTGTCGGG TTTCGCCACC   10350

TCTGACTTGA GCGTCGATTT TTGTGATGCT CGTCAGGGGG GCGGAGCCTA   10400

TGGAAAAACG CCAGCTGGCA CGACAGGTTT CCCGACTGGA AAGCGGGCAG   10450

TGAGCGCAAC GCAATTAATG TGAGTTACCT CACTCATTAG GCACCCCAGG   10500

CTTTACACTT TATGCTTCCG GCTCGTATGT TGTGTGGAAT TGTGAGCGGA   10550

TAACAATTTC ACACAGGAAA CAGCTATGAC CATGATTACG AATTAA       10596
```

( 2 ) INFORMATION FOR SEQ ID NO:16:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( x i ) SEQUENCE DESCRIPTION: SEQ ID NO:16:

```
ATGAAGGCCC CCGCTGTGCT TGCACCTGGC ATCCTCGTGC TCCTGTTTAC    50

C                                                         51
```

( 2 ) INFORMATION FOR SEQ ID NO:17:

( i ) SEQUENCE CHARACTERISTICS:
        ( A ) LENGTH: 56 bases
        ( B ) TYPE: nucleic acid
        ( C ) STRANDEDNESS: single
        ( D ) TOPOLOGY: linear ( x i ) SEQUENCE DESCRIPTION: SEQ ID NO:17:

```
CACTAGTTAG GATGGGGGAC ATGTCTGTCA GAGGATACTG CACTTGTCGG    50

CATGAA                                                    56
```

( 2 ) INFORMATION FOR SEQ ID NO:18:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:18:

TAGTACTAGC ACTATGATGT CT  22

( 2 ) INFORMATION FOR SEQ ID NO:19:

( i ) SEQUENCE CHARACTERISTICS:
    ( A ) LENGTH: 22 bases
    ( B ) TYPE: nucleic acid
    ( C ) STRANDEDNESS: single
    ( D ) TOPOLOGY: linear ( x i ) SEQUENCE DESCRIPTION: SEQ ID NO:19:

TTTACTTCTT GACGGTCCAA AG  22

( 2 ) INFORMATION FOR SEQ ID NO:20:

( i ) SEQUENCE CHARACTERISTICS:
    ( A ) LENGTH: 25 bases
    ( B ) TYPE: nucleic acid
    ( C ) STRANDEDNESS: single
    ( D ) TOPOLOGY: linear ( x i ) SEQUENCE DESCRIPTION: SEQ ID NO:20:

CAGGGGGAGT TGCAGATTCA GCTGT  25

( 2 ) INFORMATION FOR SEQ ID NO:21:

( i ) SEQUENCE CHARACTERISTICS:
    ( A ) LENGTH: 45 bases
    ( B ) TYPE: nucleic acid
    ( C ) STRANDEDNESS: single
    ( D ) TOPOLOGY: linear ( x i ) SEQUENCE DESCRIPTION: SEQ ID NO:21:

AGTTTTGTCG GTGACCTGAT CATTCTGATC TGGTTGAACT ATTAC  45